US012600713B2

(12) United States Patent
Wu et al.

(10) Patent No.: US 12,600,713 B2
(45) Date of Patent: Apr. 14, 2026

(54) CRYSTALLINE FORMS OF 6-((6,7-DIMETHOXYQUINAZOLIN-4-YL) OXY)-N,2-DIMETHYLBENZOFURAN-3-CARBOXAMIDE

(71) Applicant: HUTCHMED LIMITED, Shanghai (CN)

(72) Inventors: Zhenping Wu, Shanghai (CN); Wenji Li, Shanghai (CN); Yuping Chu, Shanghai (CN)

(73) Assignee: Hutchmed Limited, Shanghai (CN)

(*) Notice: Subject to any disclaimer, the term of this patent is extended or adjusted under 35 U.S.C. 154(b) by 0 days.

(21) Appl. No.: 18/588,874

(22) Filed: Feb. 27, 2024

(65) Prior Publication Data

US 2024/0279208 A1 Aug. 22, 2024

Related U.S. Application Data

(60) Division of application No. 17/303,114, filed on May 20, 2021, now Pat. No. 11,958,838, which is a division of application No. 16/678,760, filed on Nov. 8, 2019, now Pat. No. 11,046,674, which is a continuation of application No. 15/510,631, filed as application No. PCT/CN2015/089035 on Sep. 7, 2015, now Pat. No. 10,519,142.

(30) Foreign Application Priority Data

Sep. 10, 2014 (CN) ........................ 201410456350.9

(51) Int. Cl.
*C07D 405/12* (2006.01)
*A61P 27/02* (2006.01)
*A61P 29/00* (2006.01)
*A61P 35/00* (2006.01)

(52) U.S. Cl.
CPC ............ *C07D 405/12* (2013.01); *A61P 27/02* (2018.01); *A61P 29/00* (2018.01); *A61P 35/00* (2018.01); *C07B 2200/13* (2013.01)

(58) Field of Classification Search
CPC .................................................... C07D 405/12
See application file for complete search history.

(56) References Cited

U.S. PATENT DOCUMENTS 10,519,142 B2 12/2019 Wu et al.

FOREIGN PATENT DOCUMENTS

| | | | |
|---|---|---|---|
| CN | 101575333 | A | 11/2009 |
| JP | 2011519956 | A | 7/2011 |
| KR | 20110013381 | A | 2/2011 |
| WO | 2009137797 | A2 | 11/2009 |

OTHER PUBLICATIONS

Ashiwawa et al., "Science of Polymorphism and Crystallization of Pharmaceuticals," Maruzen Planet Corporation, pp. 272-317 (2002).
Balbach et al., "Pharmaceutical evaluation of early development candidates the 100 mg-approach," International Journal of Pharmaceutics, 275:1-12 (2004).
Braga D., "Crystal Polymorphism and Multiple Crystal Forms," 2009, Struct. Bond (2009) 132: pp. 25-50.
Caira, M.R., "Crystalline Polymorphism of Organic Compounds," Topics In Current Chemistry, 198:163-164 (1998).
Gu et al., "Preclinical pharmacokinetics and disposition of a novel selective VEGFR inhibitor Fruquintinib ( HMPL-013) and the prediction of its human pharmacokinetics," Cancer Chemother. Pharmacol, 74: 95-1, 5, (2014).
Hilfker R., "Relevance of Solid-State Properties for Pharmaceutical Product," in "Polymorphism in the pharmaceutical industry," Wiley (2006) pp. 1-19 ISBN 3-527-31146-7.
Masakuni, "Foundations and Applications of Crystal Polymorphism," CMC Publishing Co., Ltd., pp. 105-117 and pp. 181-191 (2010).
Singhal et al., "Drug polymorphism and dosage form design: a practical perspective," Advanced Drug Delivery Reviews, 56:335-347, (2004).
Sun, Q., et al. "Discovery of fruquintinib, a small molecule inhibitor of VEG FR 1, 2, 3 tyrosine kinases for cancer therapy." Cancer Biology & Therapy. (Oct. 29, 2014), vol. 15, Issue 12, pp. 1635-1645 (2014).
WIPO Application No. PCT/CN2015/089035, International Search Report, mailed Nov. 11, 2015. (5 pages).
WIPO Application No. PCT/CN2015/089035, Written Opinion of the International Searching Authority, mailed Nov. 11, 2015. (5 pages).
WIPO Application No. PCT/CN2015/089035, International Preliminary Report on Patentability, issued Mar. 14, 2017. (6 pages).

*Primary Examiner* — John S Kenyon
(74) *Attorney, Agent, or Firm* — Honigman LLP; Lucy X. Yang; Jonathan P. O'Brien

(57) ABSTRACT

The present invention relates to the pharmaceutical field, provides novel crystalline forms, solvates and the crystalline forms thereof of compound 6-((6,7-dimethoxyquinazolin-4-yl)oxy)-N,2-dimethylbenzofuran-3-carboxamide, pharmaceutical compositions, as well as the methods of preparation and the use thereof.

28 Claims, 18 Drawing Sheets

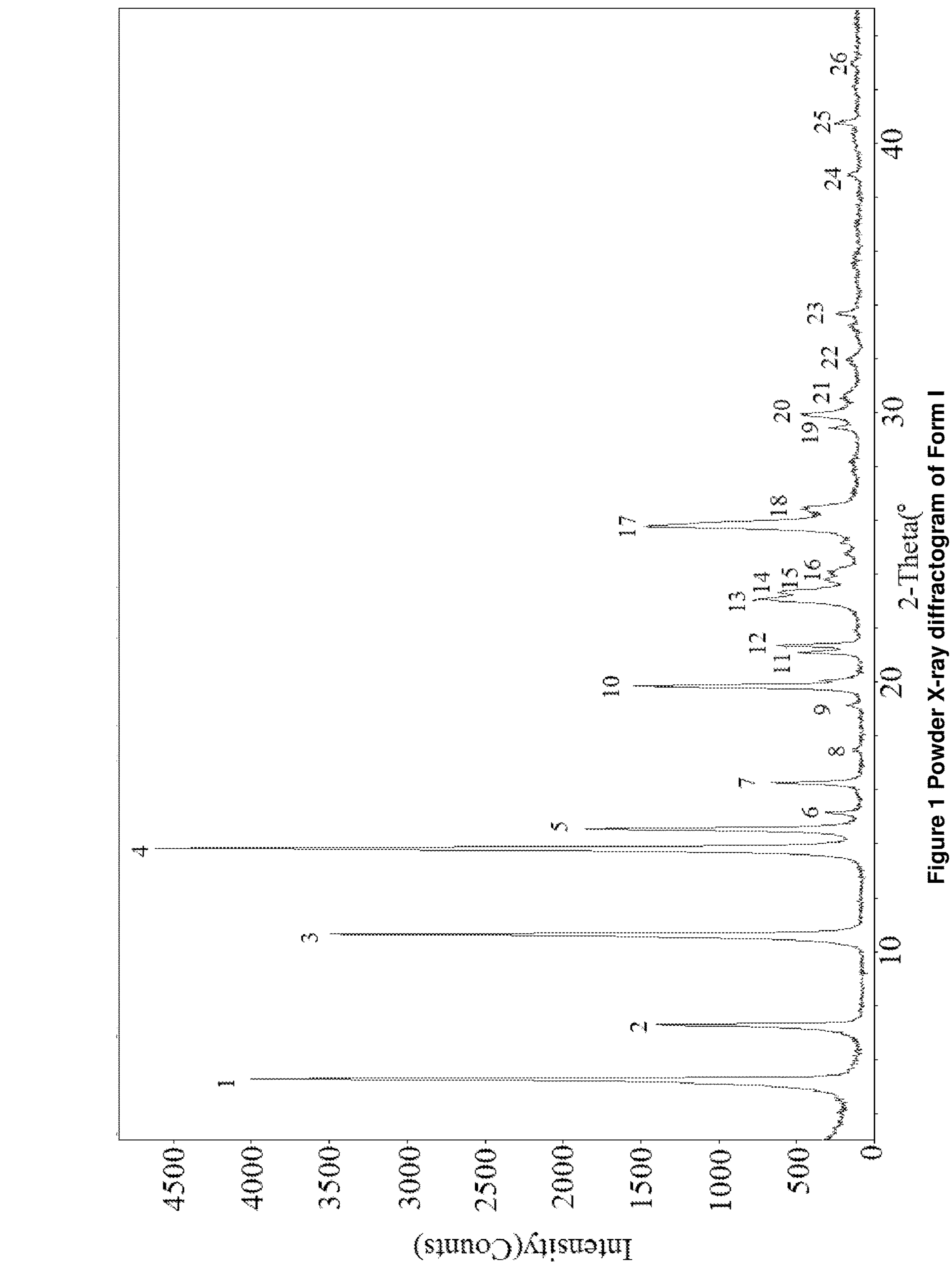
Figure 1 Powder X-ray diffractogram of Form I

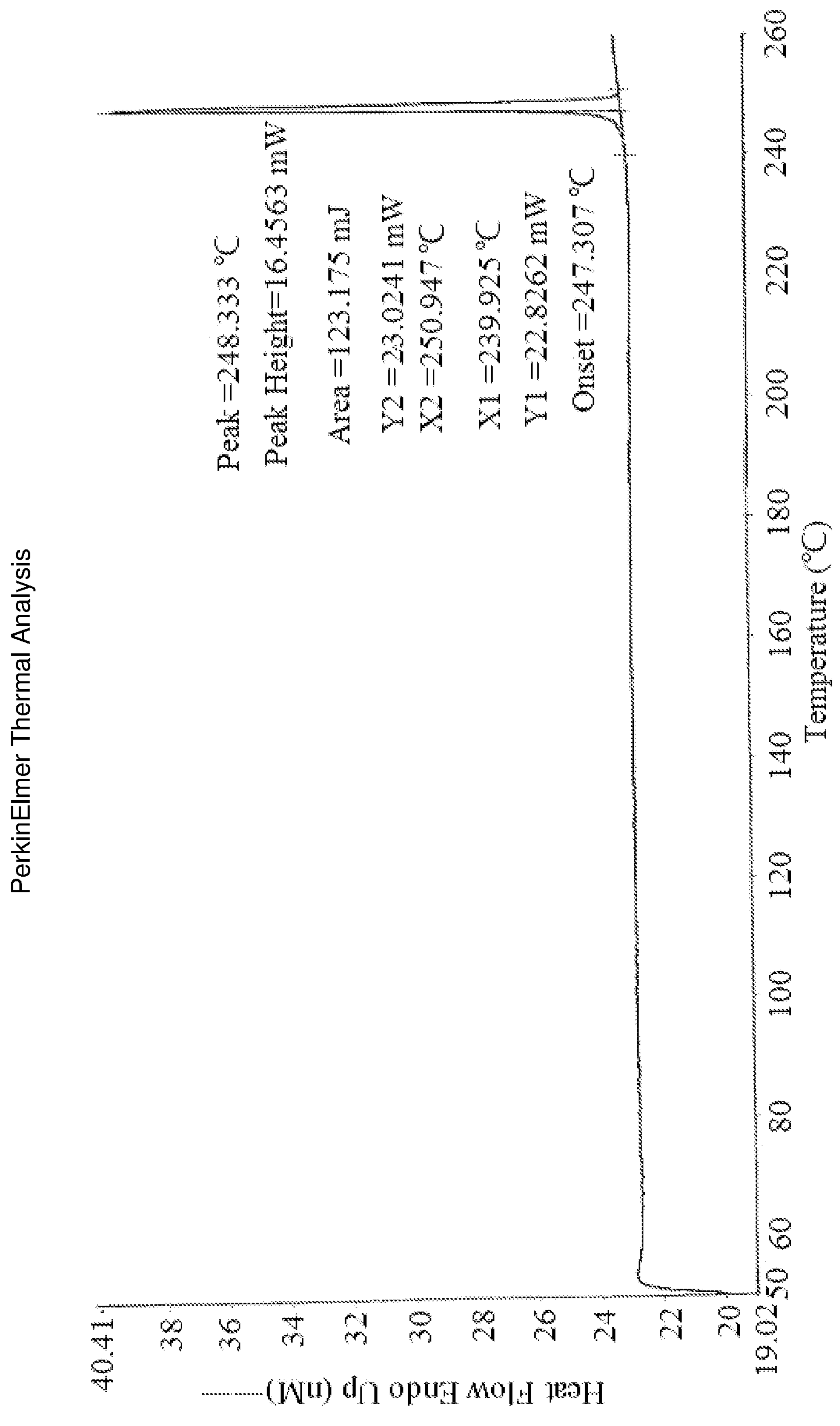
PerkinElmer Thermal Analysis
Peak = 248.333 °C
Peak Height = 16.4563 mW
Area = 123.175 mJ
Y2 = 23.0241 mW
X2 = 250.947°C
X1 = 239.925°C
Y1 = 22.8262 mW
Onset = 247.307°C
Temperature (°C)
Heat Flow Endo Up (mW)
Figure 2 Differential scanning calorimeter (DSC) thermogram of Form I

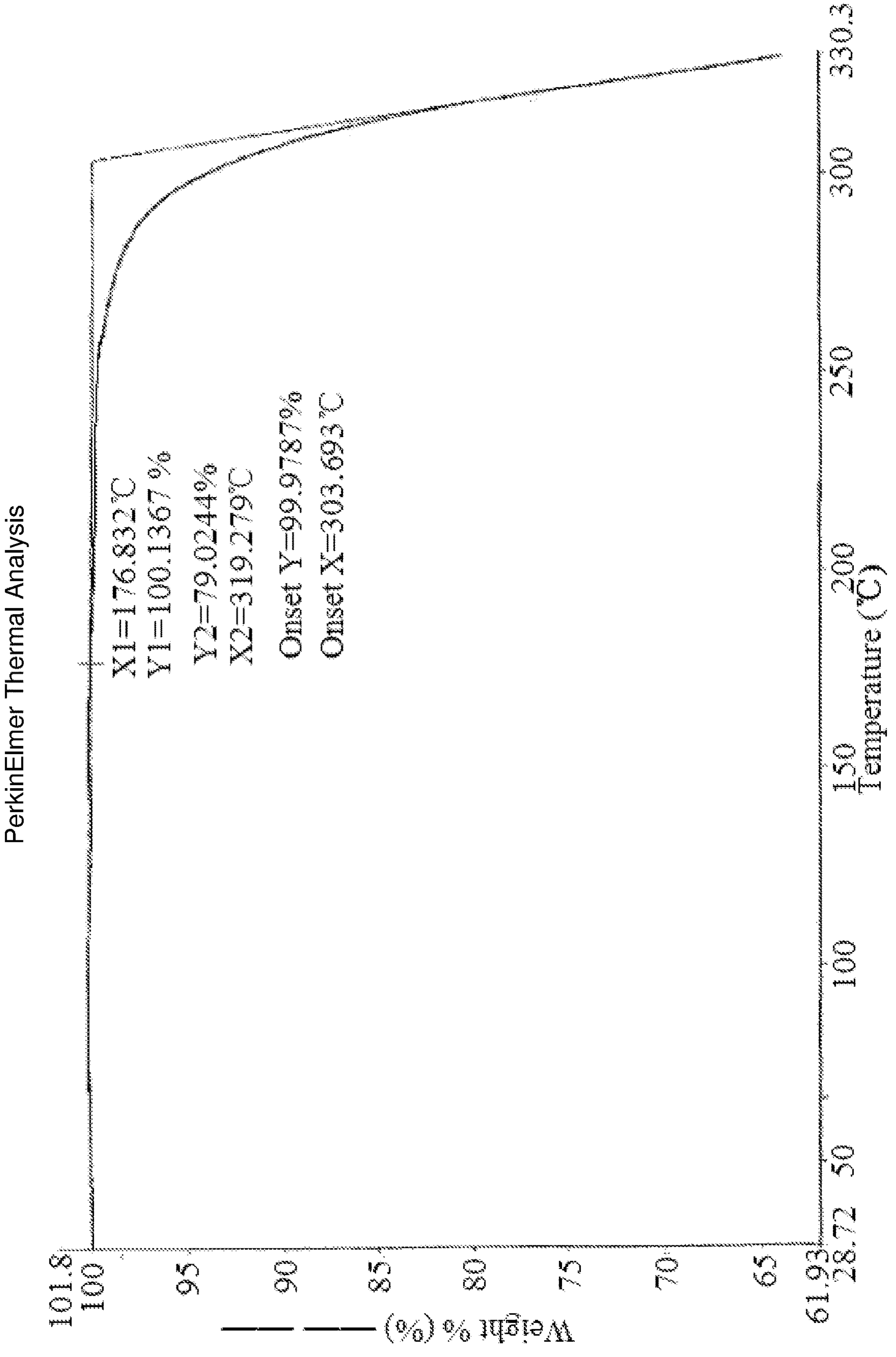
Figure 3 Thermogravimetric (TG) curve of Form I

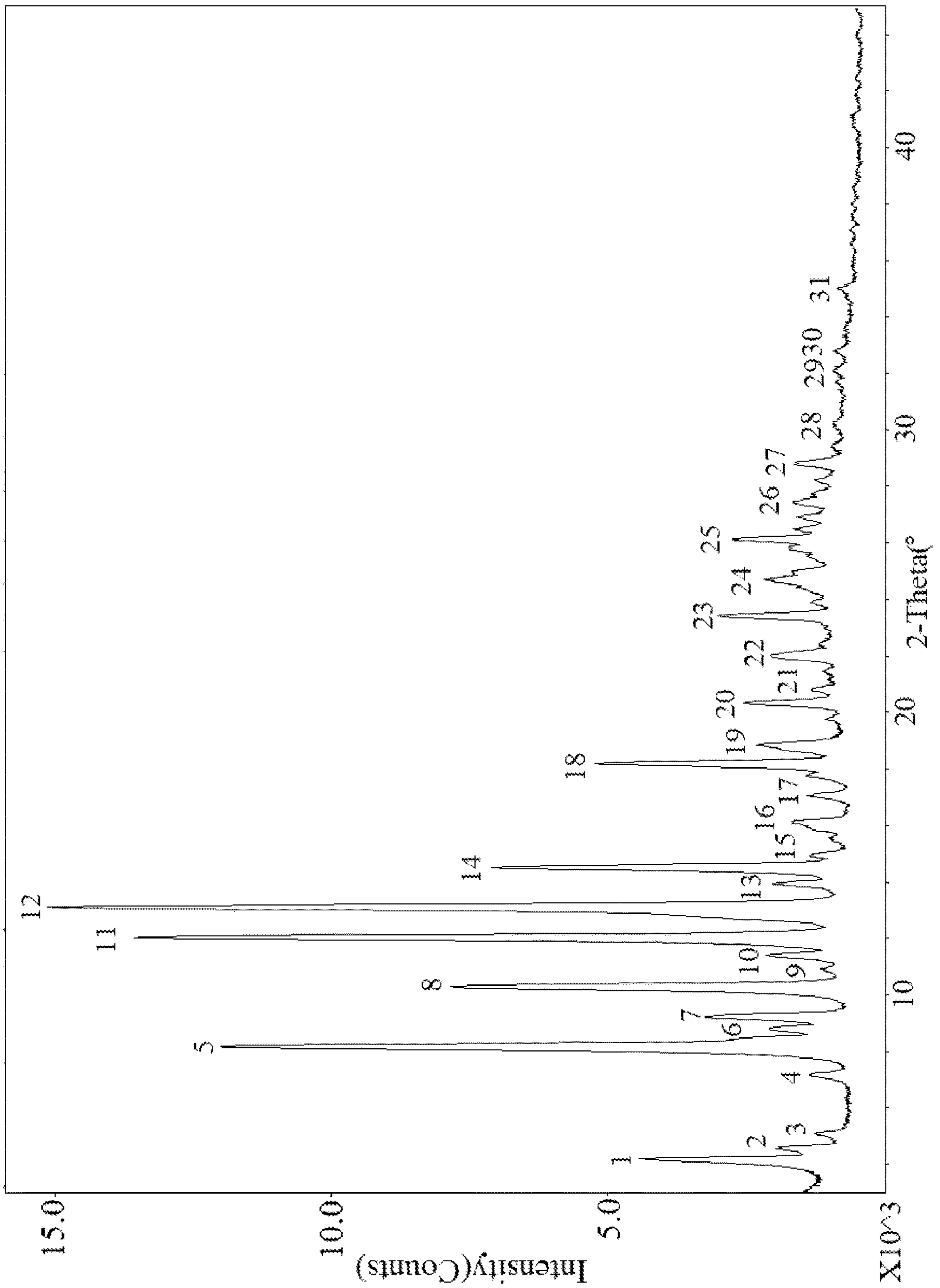
Figure 4 Powder X-ray diffractogram of Form II

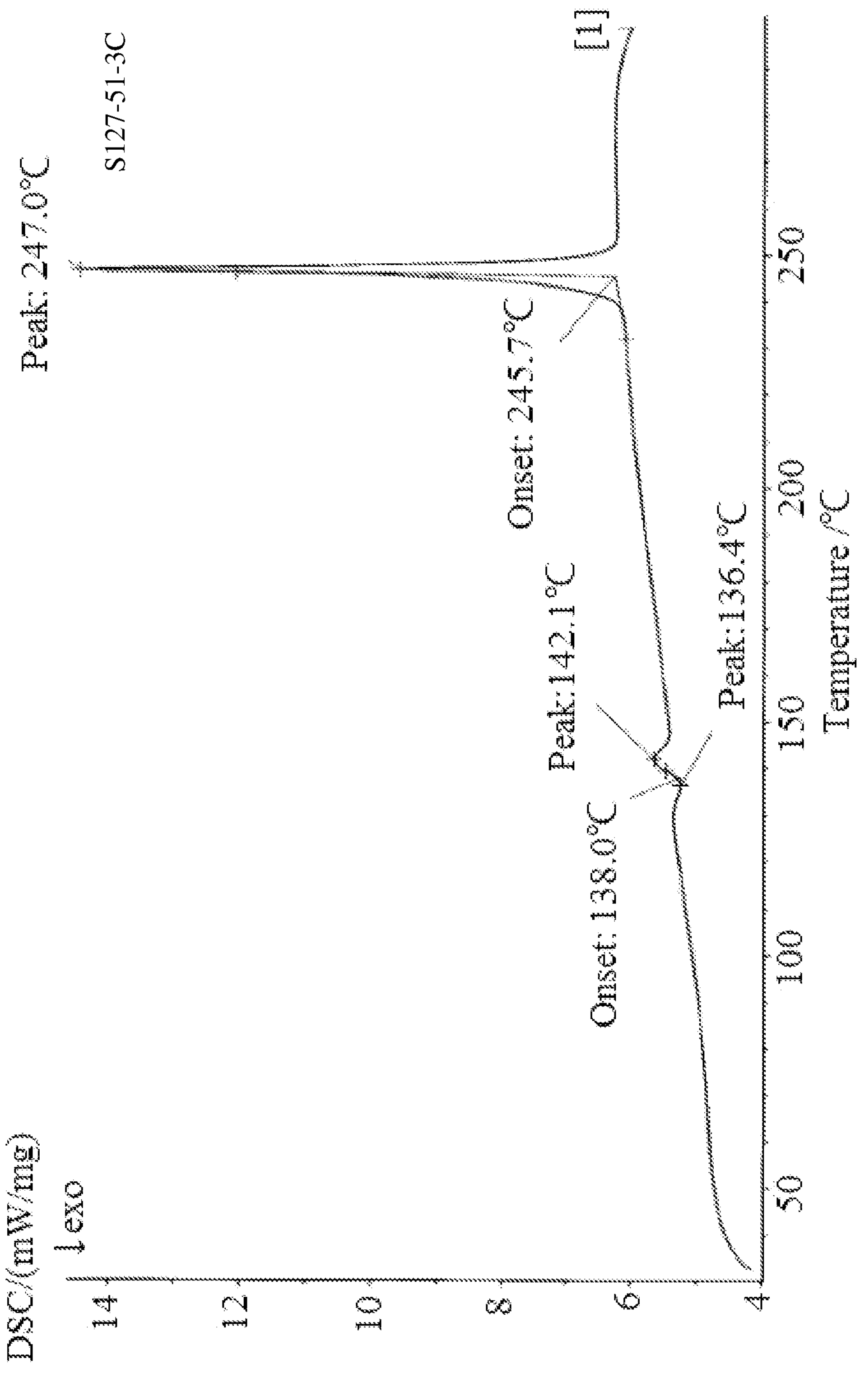
Figure 5 Differential scanning calorimeter (DSC) thermogram of Form II

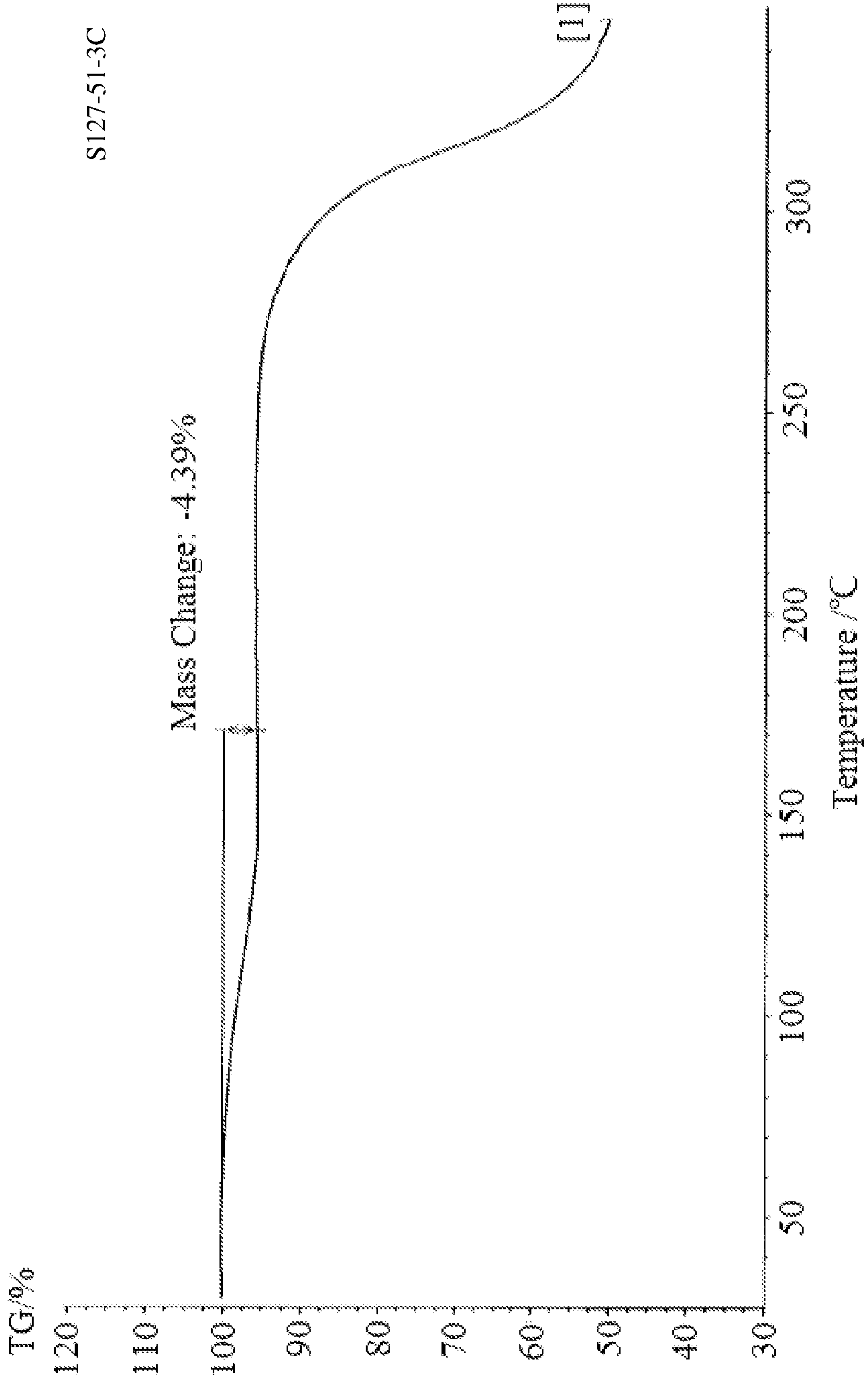
Figure 6 Thermogravimetric (TG) curve of Form II

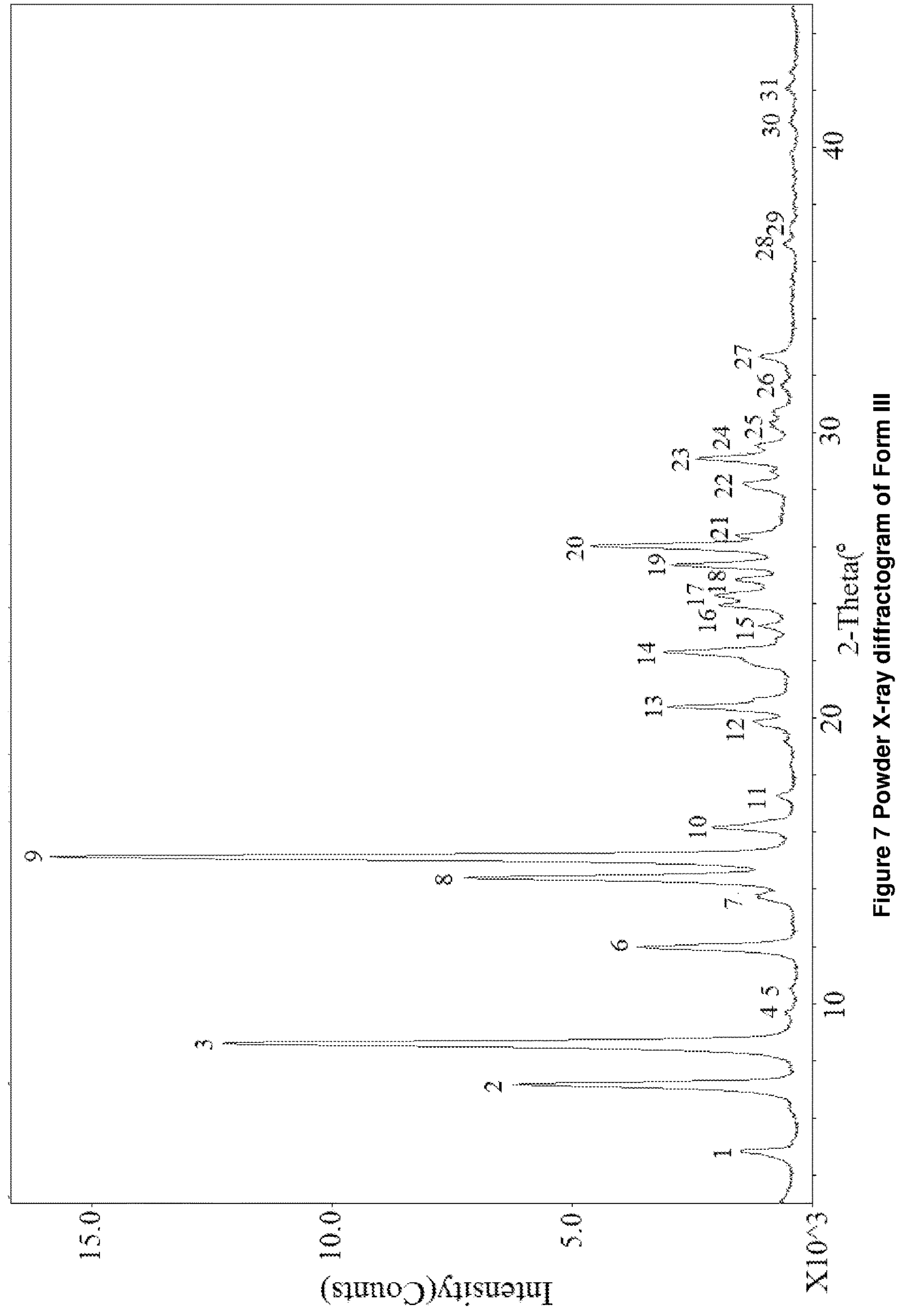
Figure 7 Powder X-ray diffractogram of Form III

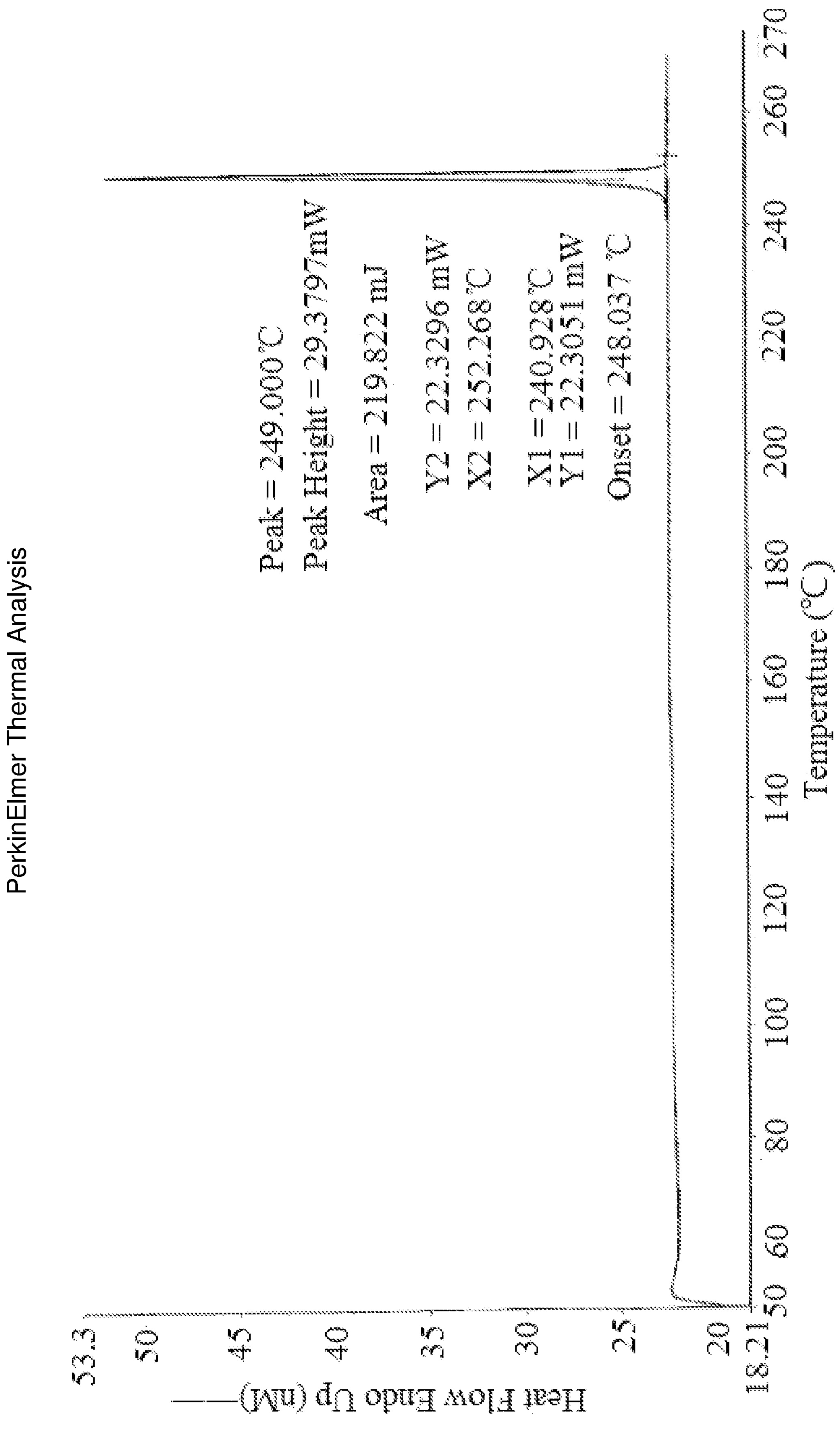
PerkinElmer Thermal Analysis
Peak = 249.000°C
Peak Height = 29.3797mW
Area = 219.822 mJ
Y2 = 22.3296 mW
X2 = 252.268°C
X1 = 240.928°C
Y1 = 22.3051 mW
Onset = 248.037°C
Figure 8 Differential scanning calorimeter (DSC) thermogram of Form III

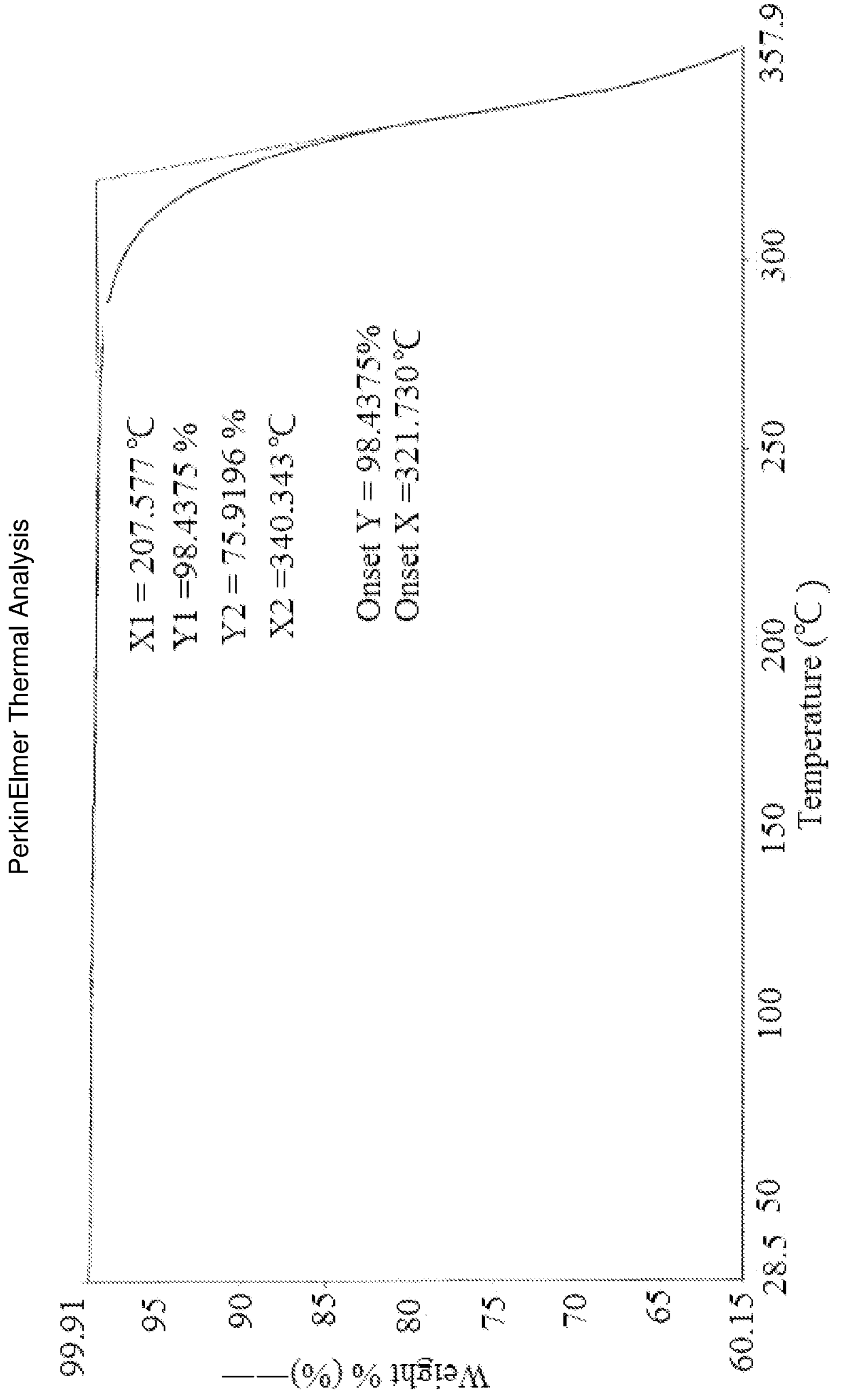
PerkinElmer Thermal Analysis
X1 = 207.577 °C
Y1 = 98.4375 %
Y2 = 75.9196 %
X2 = 340.343°C
Onset Y = 98.4375%
Onset X = 321.730°C
Temperature (°C)
Weight % (%) ——
Figure 9 Thermogravimetric (TG) curve of Form III

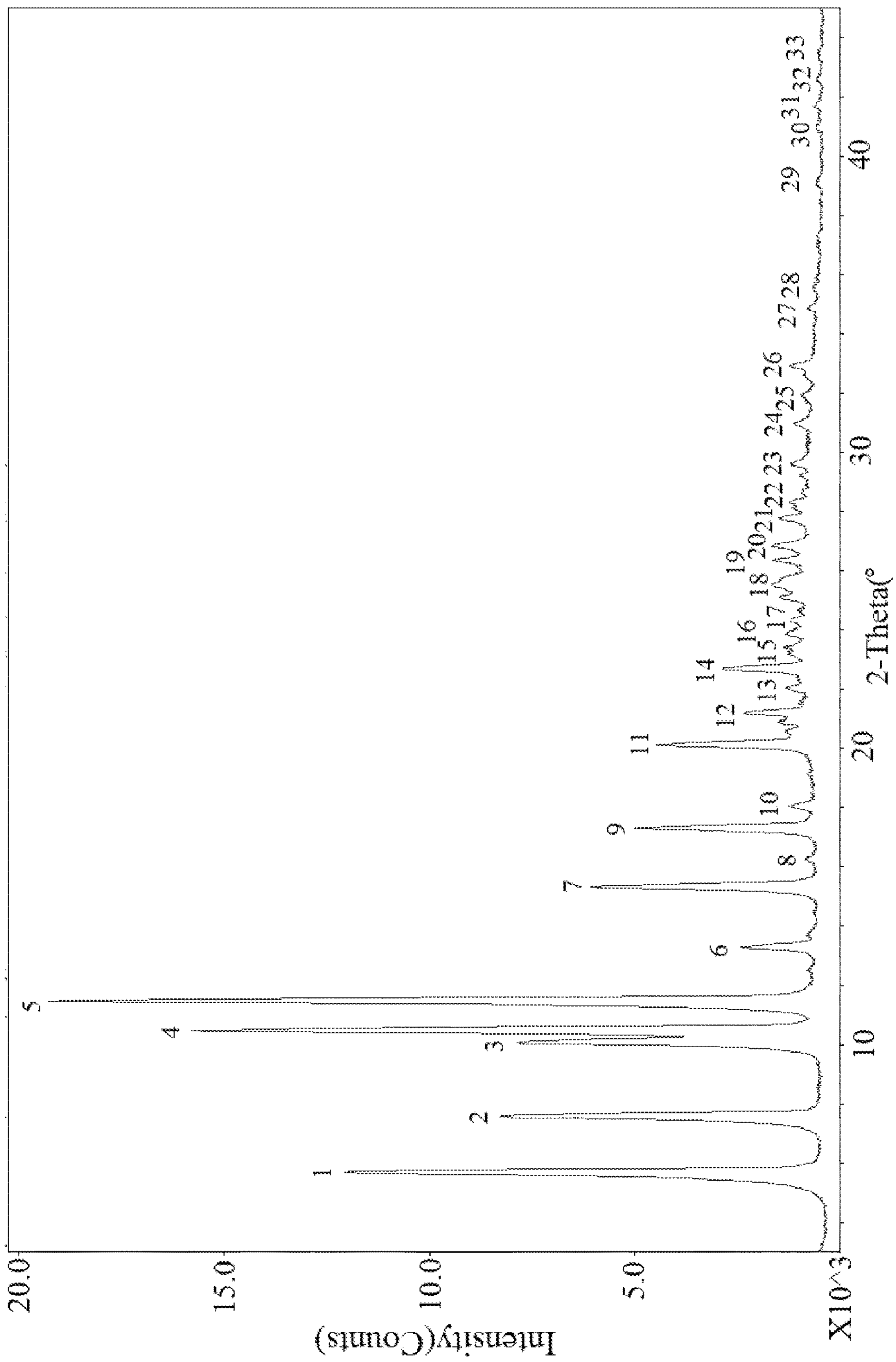
Figure 10 Powder X-ray diffractogram of Form IV

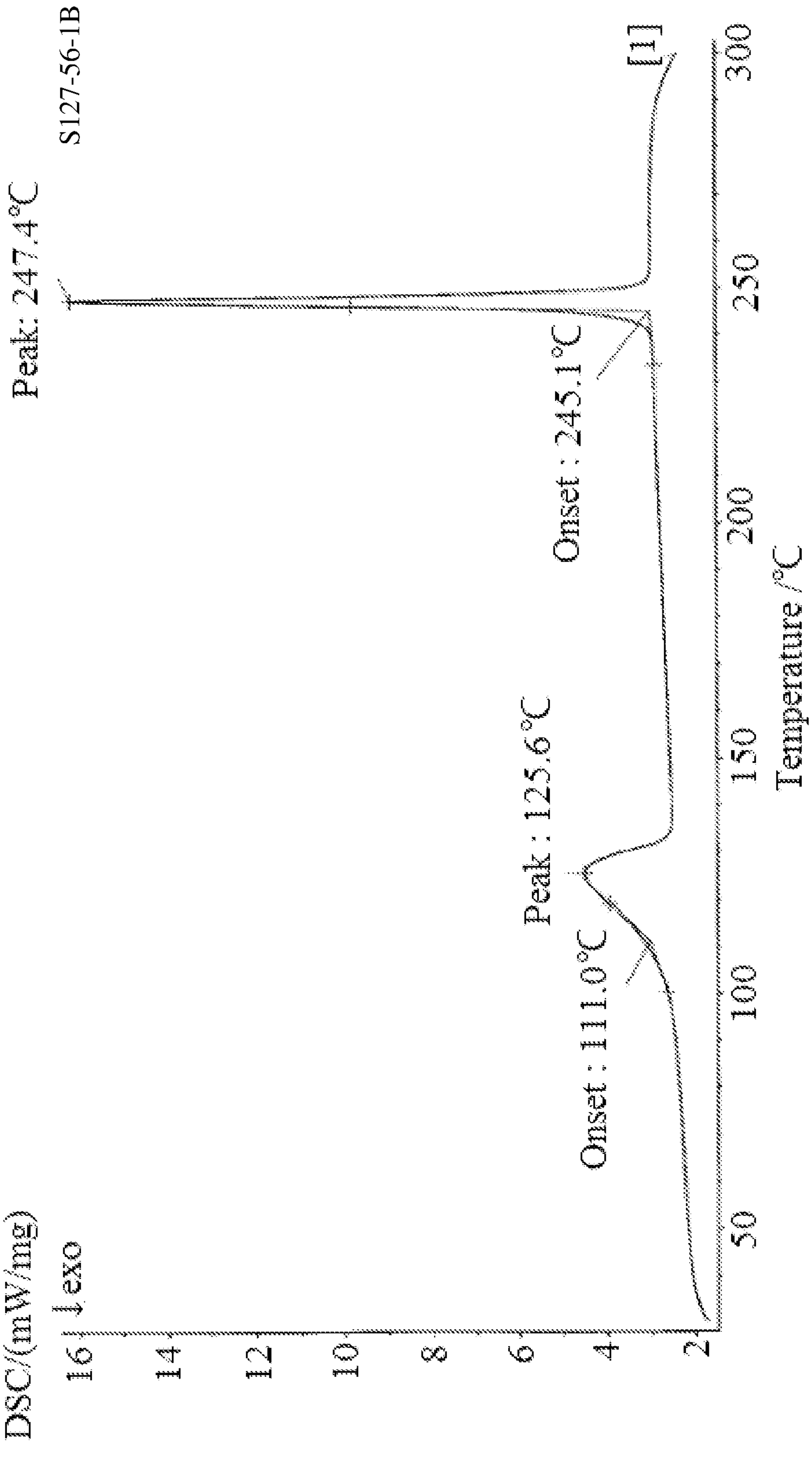
Figure 11 Differential scanning calorimeter (DSC) thermogram of Form IV

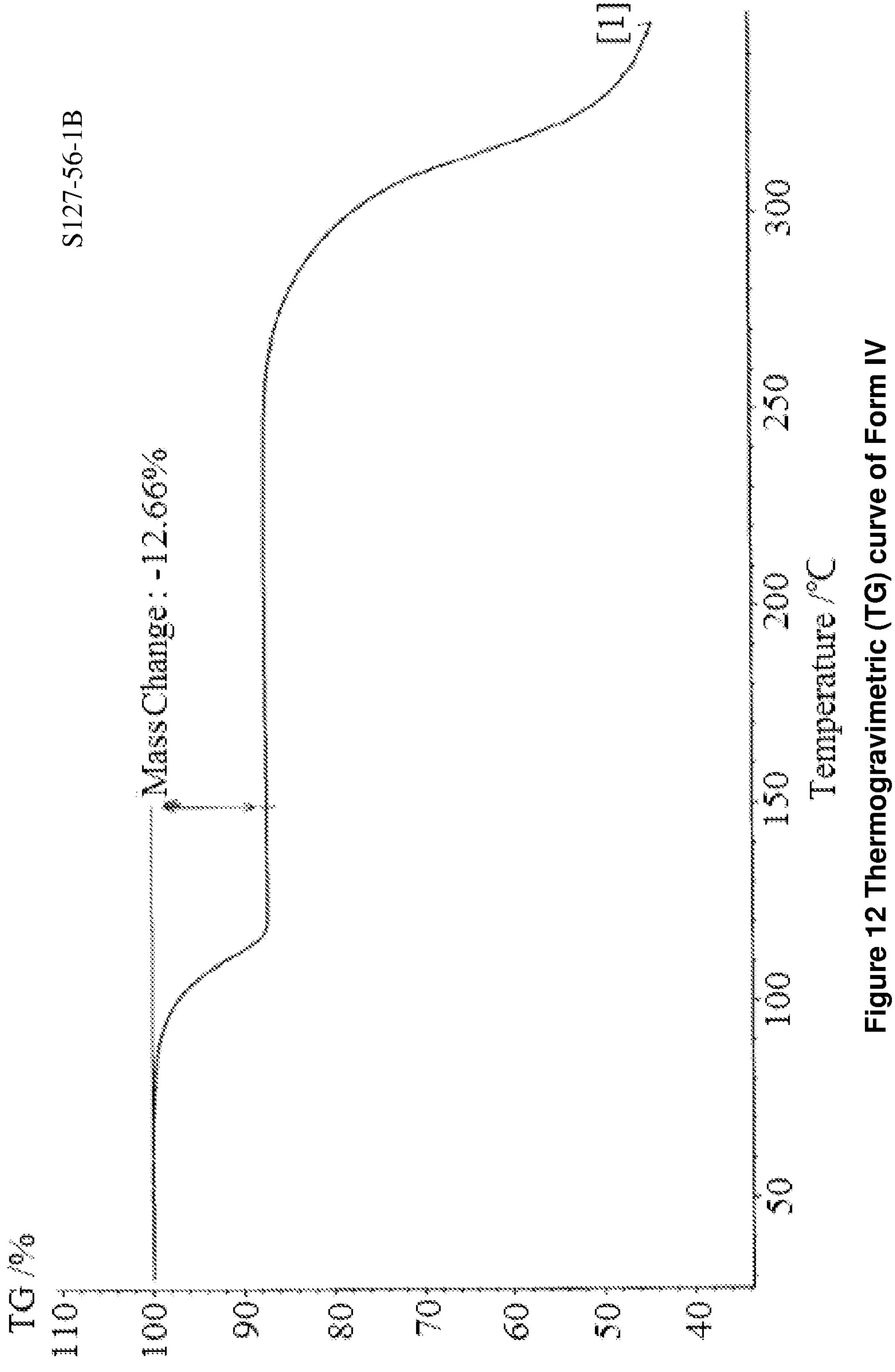
Figure 12 Thermogravimetric (TG) curve of Form IV

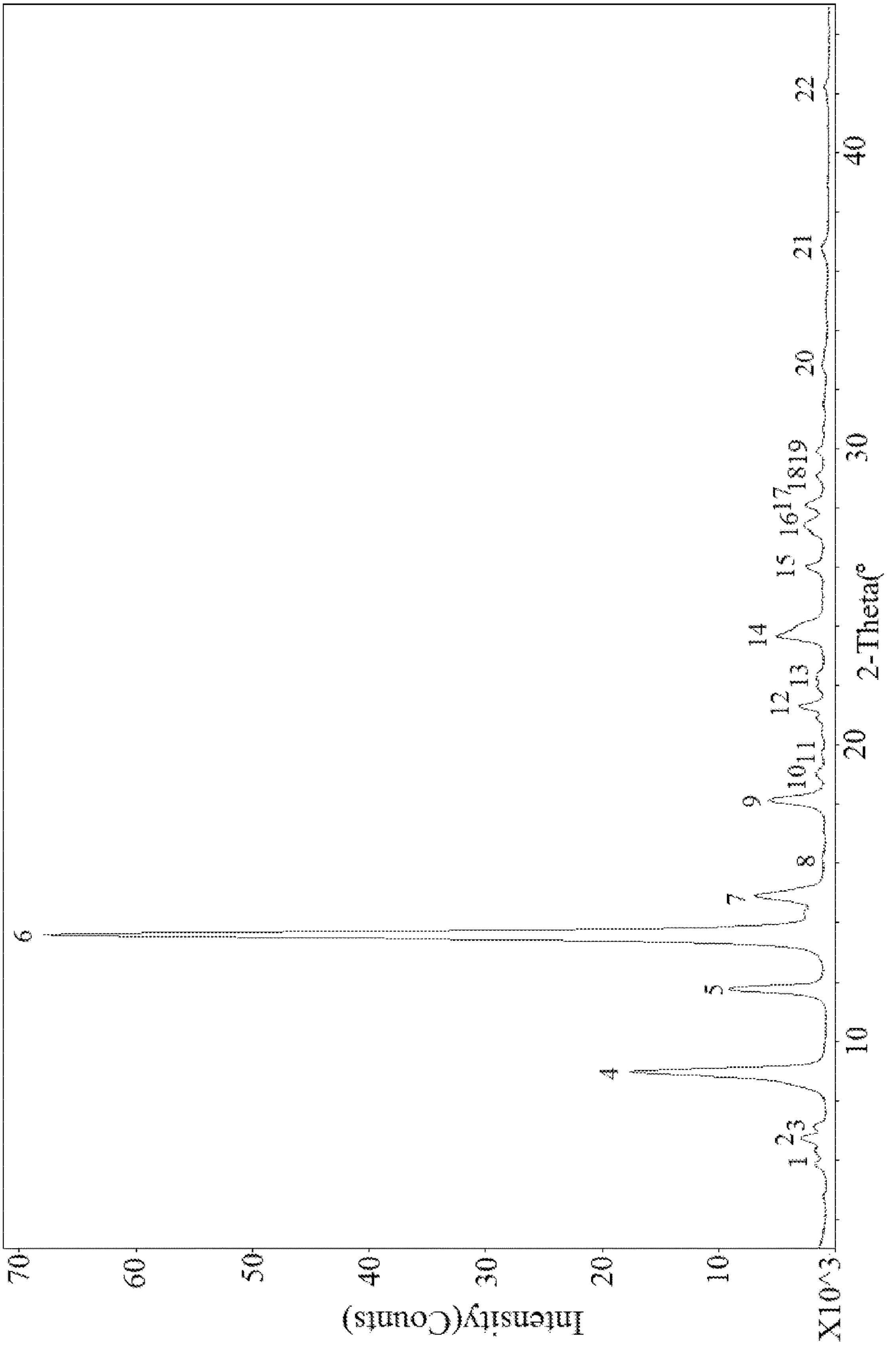
Figure 13 Powder X-ray diffractogram of Form VII

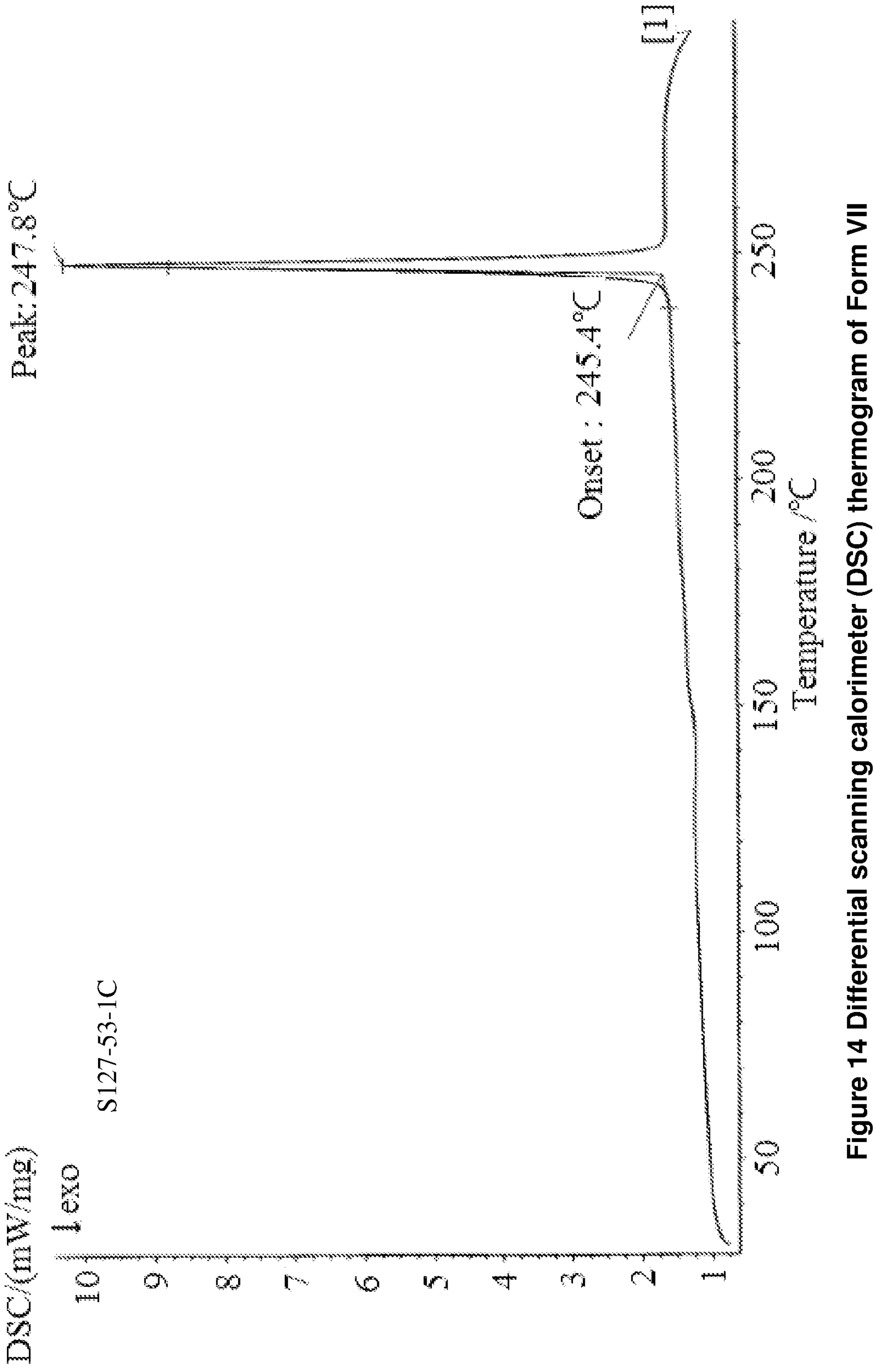
Figure 14 Differential scanning calorimeter (DSC) thermogram of Form VII

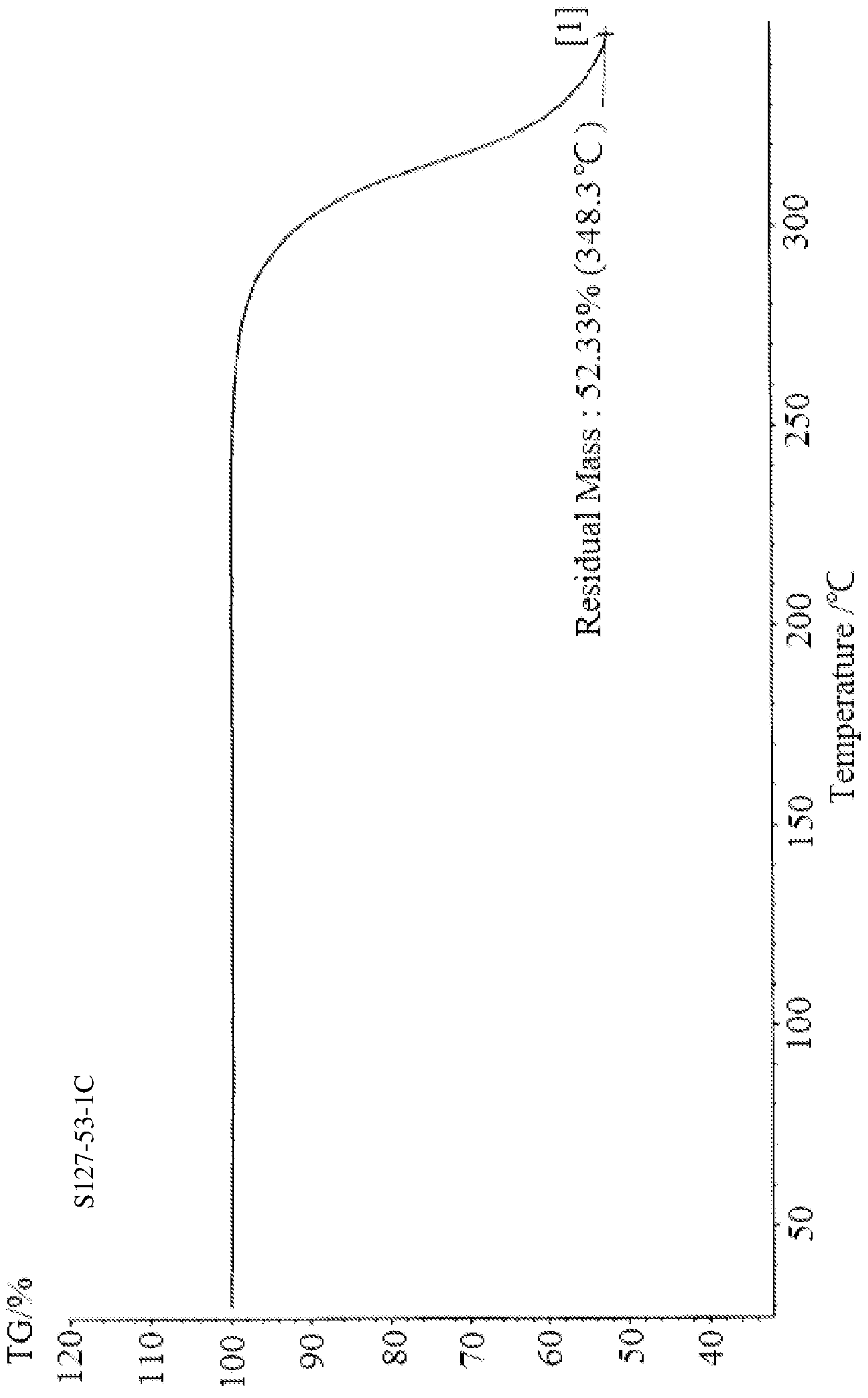
Figure 15 Thermogravimetric (TG) curve of Form VII

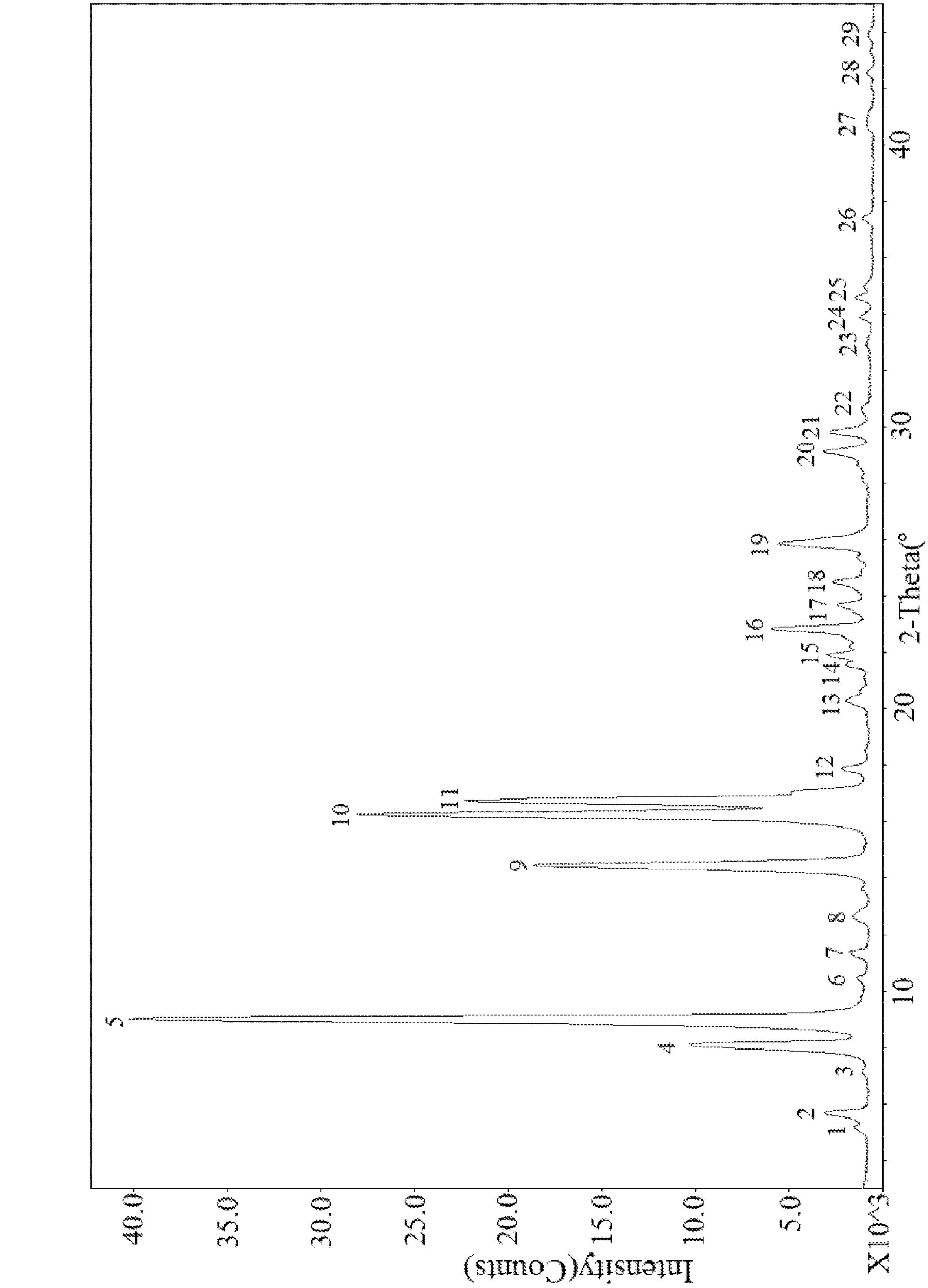
Figure 16 Powder X-ray diffractogram of Form VIII

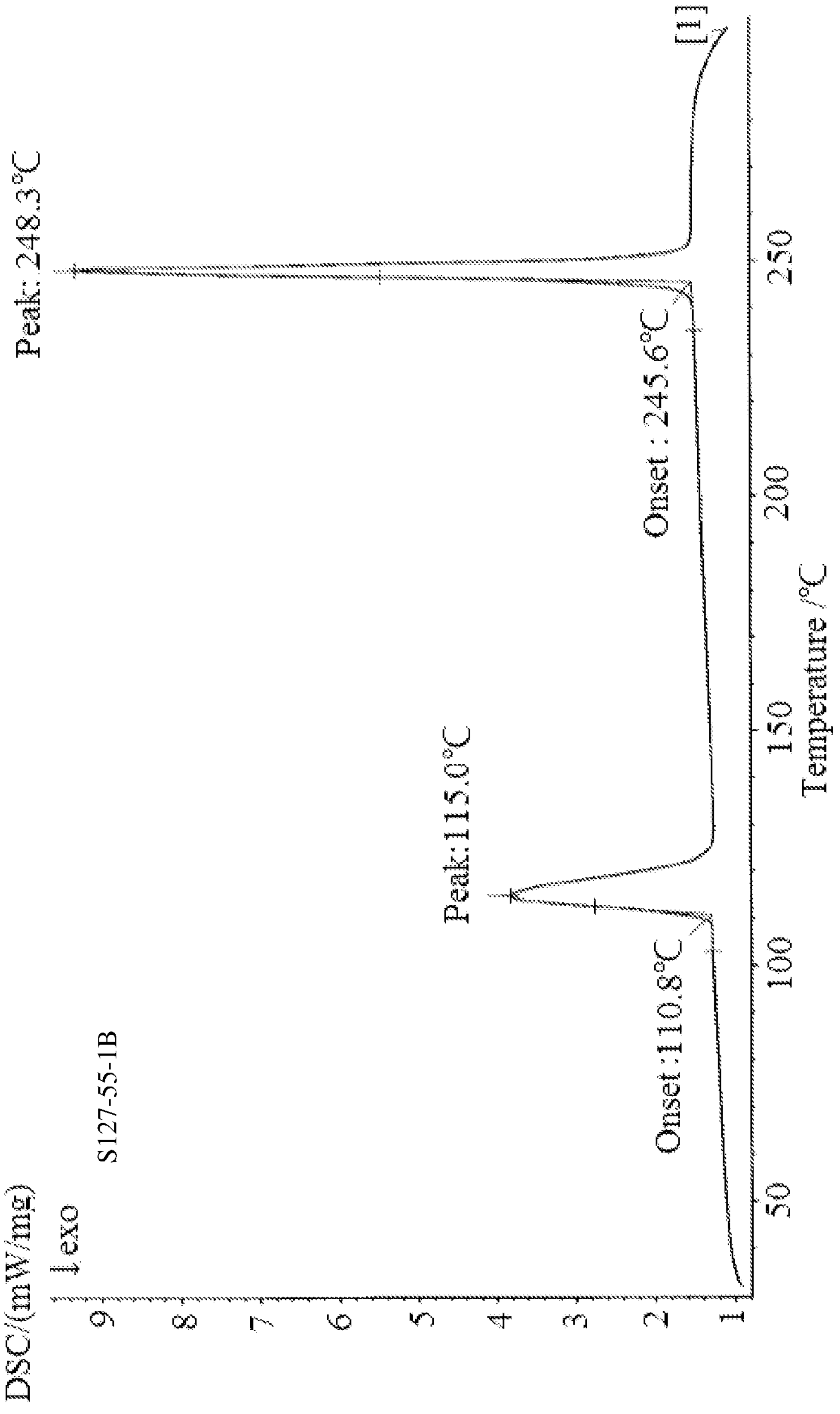
Figure 17 Differential scanning calorimeter (DSC) thermogram of Form VIII

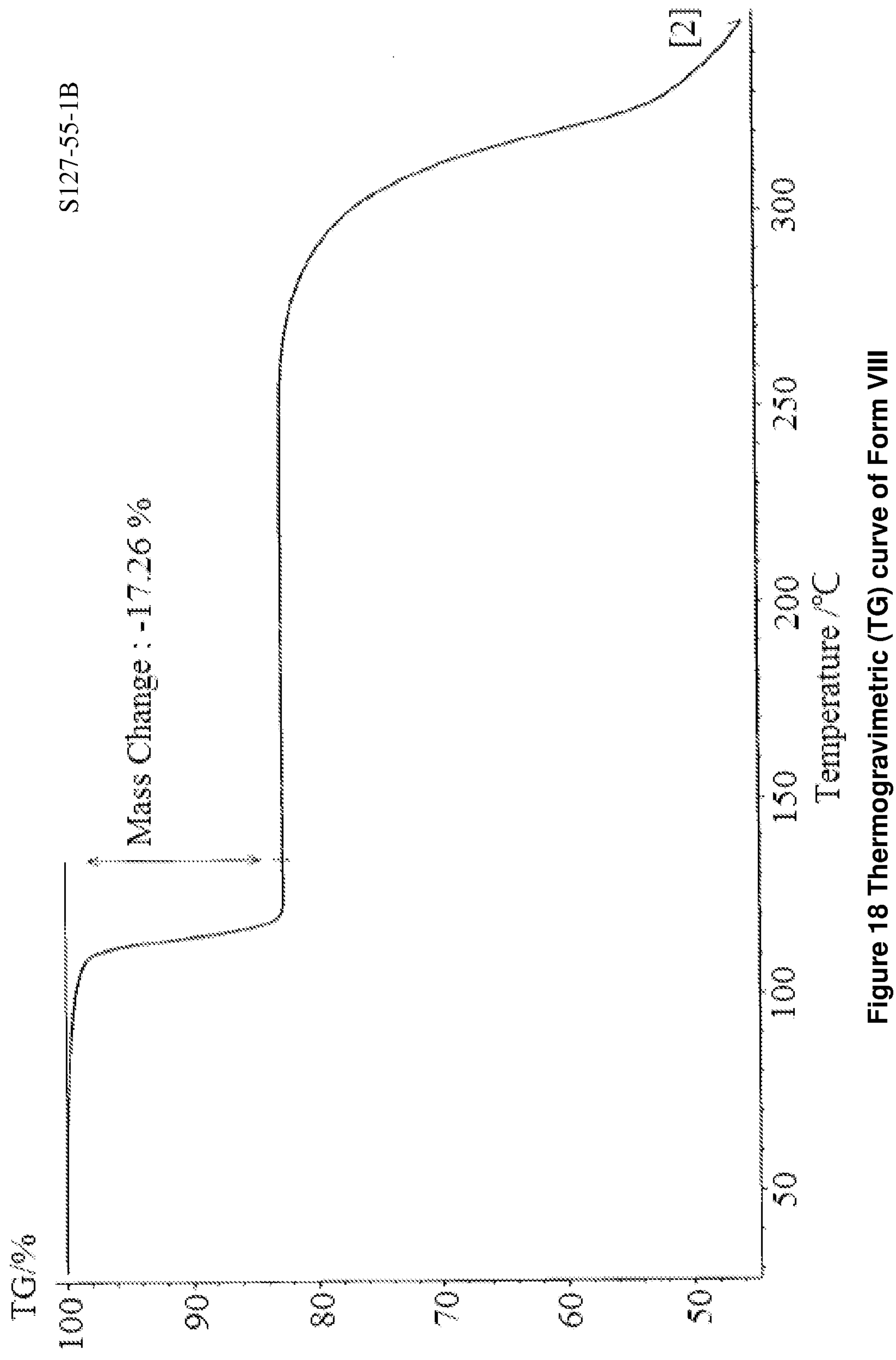
Figure 18 Thermogravimetric (TG) curve of Form VIII

CRYSTALLINE FORMS OF 6-((6,7-DIMETHOXYQUINAZOLIN-4-YL)OXY)-N,2-DIMETHYLBENZOFURAN-3-CARBOXAMIDE

CROSS REFERENCE TO RELATED APPLICATIONS

This application is a division of U.S. patent application Ser. No. 17/303,114, filed May 20, 2021, which is a division of U.S. application Ser. No. 16/678,760, filed Nov. 8, 2019, now U.S. Pat. No. 11,046,674, issued Jun. 29, 2021, which is a continuation of U.S. application Ser. No. 15/510,631, filed Mar. 10, 2017, now U.S. Pat. No. 10,519,142, issued Dec. 31, 2019, which is the national stage entry under 35 U.S.C. § 371 of International Application No. PCT/CN2015/089035, filed Sep. 7, 2015, which claims priority to Chinese Patent Application No. 201410456350.9, filed Sep. 10, 2014; the contents of these applications are each incorporated herein by reference in their entirety.

FIELD OF THE INVENTION

The present invention relates to the pharmaceutical field, provides novel crystalline forms, solvates and the crystalline forms thereof of compound 6-((6,7-dimethoxyquinazolin-4-yl)oxy)-N,2-dimethylbenzofuran-3-carboxamide, pharmaceutical compositions comprising the novel crystalline forms, as well as the methods of preparation and the use thereof.

BACKGROUND OF THE INVENTION

The compound 6-((6,7-dimethoxyquinazolin-4-yl)oxy)-N,2-dimethylbenzofuran-3-carboxamide describe herein, with the chemical structure of Formula A, shows KDR kinase inhibition activities. Vascular endothelial growth factor (VEGF), and its receptor VEGFR-2, also known as kinase insert domain-containing receptor (KDR), constitute an important angiogenic pathway. Studies have shown that inhibition of KDR can cause apoptosis of endothelial cells, which consequently block the angiogenesis process (Rubin M. Tuder, Chest, 2000; 117: 281). Thus, KDR inhibitors can be used for treating angiogenesis-related disorders, such as cancer, age-related macular degeneration and chronic inflammory disease. Studies have shown that compound 6-((6,7-dimethoxyquinazolin-4-yl)oxy)-N,2-dimethylbenzofuran-3-carboxamide can be used for treating angiogenesis-related disorders, such as the treatment of cancer.

Formula A

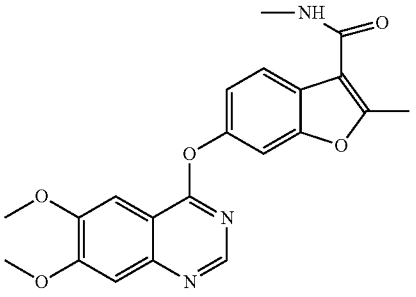

The ability of a compound to exist in at least one crystal structure or solid state form is known as polymorphism. Many compounds may exist as polymorph crystals and those compounds may also exist in a solid amorphous state. Until polymorphism of a compound is discovered, it is highly unpredictable (1) whether a particular compound will exhibit polymorphism, (2) how to make any such unknown polymorphs, and (3) what the properties, such as stability, will be of any such unknown polymorphs. See, e.g., J. Bernstein "Polymorphism in Molecular Crystals", Oxford University Press, (2002).

Because the properties of any solid material depend on the structure as well as on the nature of the compound itself, different solid state forms of a compound can and often do exhibit different physical and chemical properties. Differences in chemical properties can be determined through a variety of analytical techniques to be used to characterize, analyze, and compare. And those differences in chemical properties may ultimately be used to differentiate among different solid state forms that may be discovered to exist. Furthermore, differences in physical properties, such as solubility and bioavailability, of solid state forms can be important when formulating a pharmaceutical compound. As such, novel crystalline and amorphous solid state forms of pharmaceutical compounds, such as the compound of Formula A, can be important in the development of such compounds.

The compound 6-((6,7-dimethoxyquinazolin-4-yl)oxy)-N,2-dimethylbenzofuran-3-carboxamide was first described in patent WO 2009/137797 A2, and the methods of preparation thereof were also described therein.

SUMMARY OF THE INVENTION

After a lot of exploration and research, we have found that the compound of Formula A (6-((6,7-dimethoxyquinazolin-4-yl)oxy)-N,2-dimethylbenzofuran-3-carboxamide) can exist in different crystalline forms, and can form solvates with certain solvents. The existence of various polymorphic forms of the compound of Formula A is explored in order to determine and prepare the most appropriate form of the compound for the pharmaceutical use. Based on these studies, the present invention provides the compound of Formula A in new crystalline forms, solvates and the crystalline forms thereof, which are designated Form I, Form II, Form III, Form IV, Form VII, and Form VIII respectively.

In one aspect, the present invention provides novel crystalline forms of the compound of Formula A or the solvates thereof, which are crystalline, non-hygroscopic and stable.

Firstly, provided herein is Form I of 6-((6,7-dimethoxyquinazolin-4-yl)oxy)-N,2-dimethylbenzofuran-3-carboxamide, i.e. Form I of the compound of Formula A.

Secondly, provided herein are solvates of 6-((6,7-dimethoxyquinazolin-4-yl)oxy)-N,2-dimethylbenzofuran-3-carboxamide, which are ethanol solvate, acetic acid solvate and dioxane solvate of the compound of Formula A.

Further, provided herein are solvates of 6-((6,7-dimethoxyquinazolin-4-yl)oxy)-N,2-dimethylbenzofuran-3-carboxamide, which are hemiethanol solvate, monoacetic acid solvate and monodioxane solvate of the compound of Formula A.

Even further, provided herein is hemiethanol solvate of 6-((6,7-dimethoxyquinazolin-4-yl)oxy)-N,2-dimethylbenzofuran-3-carboxamide, which is Form II of the compound of Formula A.

Even further, provided herein is Form III of 6-((6,7-dimethoxyquinazolin-4-yl)oxy)-N,2-dimethylbenzofuran-3-carboxamide, i.e. Form III of the compound of Formula A.

Even further, provided herein is monoacetic acid solvate of 6-((6,7-dimethoxyquinazolin-4-yl)oxy)-N,2-dimethylbenzofuran-3-carboxamide, which is Form IV of the compound of Formula A.

Even further, provided herein is Form VII of 6-((6,7-dimethoxyquinazolin-4-yl)oxy)-N,2-dimethylbenzofuran-3-carboxamide, i.e. Form VII of the compound of Formula A.

Even further, provided herein is monodioxane solvate of 6-((6,7-dimethoxyquinazolin-4-yl)oxy)-N,2-dimethylbenzofuran-3-carboxamide, which is Form VIII of the compound of Formula A.

In another aspect, the present invention provides methods of preparation for the crystalline forms of the compound of Formula A, the solvates of the compound of Formula A and the crystalline forms thereof (such as Form I, Form II, Form III, Form IV, Form VII and Form VIII), which are reproducible and easy in operation.

In still another aspect, the present invention provides pharmaceutical compositions comprising an effective amount of any one or more of the crystalline forms of the compound of Formula A, the solvates of the compound of Formula A and the crystalline forms thereof (such as Forms I, Form II, Form III, Form IV, Form VII, and Form VIII), and at least one pharmaceutically acceptable carrier.

Also provided herein is a method of treating diseases associated with KDR inhibition, for example angiogenesis-related disorders, such as, cancer, age-related macular degeneration and chronic inflammory disease, in a subject in recognized need thereof. The method comprises administering to said subject in need thereof an effective amount of the compound of Formula A and/or pharmaceutically acceptable salts thereof, wherein the compound of Formula A exists in one or more forms of the crystalline forms of the compound of Formula A, and/or the solvates of the compound of Formula A or the crystalline forms thereof described herein, such as Forms I, Form II, Form III, Form IV, Form VII, or FormVIII.

Also provided herein is a use of the crystalline forms of the compound of Formula A, and/or the solvates of the compound of Formula A or the crystalline forms thereof (such as Forms I, Form II, Form III, Form IV, Form VII, or FormVIII) in the manufacture of a medicament for treating angiogenesis-related disorders. In some embodiments, said angiogenesis-related disorders are selected from cancer, age-related macular degeneration and chronic inflammory disease.

BRIEF DESCRIPTION OF THE DRAWINGS

FIG. 1 shows a powder X-ray diffractogram of Form I of the compound of Formula A, the horizontal axis (x-axis) plots the diffraction 2 theta, and the vertical axis (y-axis) plots the intensity (counts).

FIG. 2 shows a differential scanning calorimeter (DSC) thermogram of Form I of the compound of Formula A, the horizontal axis (x-axis) plots the temperature (° C.), and the vertical axis (y-axis) plots the heat flow (mW).

FIG. 3 shows a Thermogravimetric (TG) curve of Form I of the compound of Formula A, the horizontal axis (x-axis) plots the temperature (° C.), and the vertical axis (y-axis) plots the weight percentage (%).

FIG. 4 shows a powder X-ray diffractogram of Form II of hemiethanol solvate of the compound of Formula A, the horizontal axis (x-axis) plots the diffraction 2 theta, and the vertical axis (y-axis) plots the intensity (counts).

FIG. 5 shows a differential scanning calorimeter (DSC) thermogram of Form II of hemiethanol solvate of the compound of Formula A, the horizontal axis (x-axis) plots the temperature (° C.), and the vertical axis (y-axis) plots the heat flow (mW).

FIG. 6 shows a Thermogravimetric (TG) curve of Form II of hemiethanol solvate of the compound of Formula A, the horizontal axis (x-axis) plots the temperature (° C.), and the vertical axis (y-axis) plots the weight percentage (%).

FIG. 7 shows a powder X-ray diffractogram of Form III of the compound of Formula A, the horizontal axis (x-axis) plots the diffraction 2 theta, and the vertical axis (y-axis) plots the intensity (counts).

FIG. 8 shows a differential scanning calorimeter (DSC) thermogram of Form III of the compound of Formula A, the horizontal axis (x-axis) plots the temperature (° C.), and the vertical axis (y-axis) plots the heat flow (mW).

FIG. 9 shows a Thermogravimetric (TG) curve of Form III of the compound of Formula A, the horizontal axis (x-axis) plots the temperature (° C.), and the vertical axis (y-axis) plots the weight percentage (%).

FIG. 10 shows a powder X-ray diffractogram of Form IV of monoacetic acid solvate of the compound of Formula A, the horizontal axis (x-axis) plots the diffraction 2 theta, and the vertical axis (y-axis) plots the intensity (counts).

FIG. 11 shows a differential scanning calorimeter (DSC) thermogram of Form IV of monoacetic acid solvate of the compound of Formula A, the horizontal axis (x-axis) plots the temperature (° C.), and the vertical axis (y-axis) plots the heat flow (mW).

FIG. 12 shows a Thermogravimetric (TG) curve of Form IV of monoacetic acid solvate of the compound of Formula A, the horizontal axis (x-axis) plots the temperature (° C.), and the vertical axis (y-axis) plots the weight percentage (%).

FIG. 13 shows a powder X-ray diffractogram of Form VII of the compound of Formula A, the horizontal axis (x-axis) plots the diffraction 2 theta, and the vertical axis (y-axis) plots the intensity (counts).

FIG. 14 shows a differential scanning calorimeter (DSC) thermogram of Form VII of the compound of Formula A, the horizontal axis (x-axis) plots the temperature (° C.), and the vertical axis (y-axis) plots the heat flow (mW).

FIG. 15 shows a Thermogravimetric (TG) curve of Form VII of the compound of Formula A, the horizontal axis (x-axis) plots the temperature (° C.), and the vertical axis (y-axis) plots the weight percentage (%).

FIG. 16 shows a powder X-ray diffractogram of Form VIII of monodioxane solvate of the compound of Formula A, the horizontal axis (x-axis) plots the diffraction 2 theta, and the vertical axis (y-axis) plots the intensity (counts).

FIG. 17 shows a differential scanning calorimeter (DSC) thermogram of Form VIII of monodioxane solvate of the compound of Formula A, the horizontal axis (x-axis) plots the temperature (° C.), and the vertical axis (y-axis) plots the heat flow (mW).

FIG. 18 shows a Thermogravimetric (TG) curve of Form VIII of monodioxane solvate of the compound of Formula A, the horizontal axis (x-axis) plots the temperature (° C.), and the vertical axis (y-axis) plots the weight percentage (%).

DEFINITIONS

Unless indicated otherwise, as used in the present application (including the specification and the claims), the following abbreviations or terms have the meanings as set forth below. It must be noted that the singular forms "a", "an," and "the" include plural referents, except to the extent that the context clearly indicates not.

The term "crystalline form of the present invention" as used herein refers to crystalline forms Form I, Form II, Form III, Form IV, Form VII or Form VIII of the compound of Formula A or the solvates thereof, as well as mixtures thereof. "Form", "crystalline form" and "polymorph," may be used interchangeably herein.

The term "compound of Formula A", or "6-((6,7-dimethoxyquinazolin-4-yl)oxy)-N,2-dimethylbenzofuran-3-carboxamide" as used herein, refers to a compound with the following chemical structure of Formula A (also referenced as "Compound A"):

Formula A

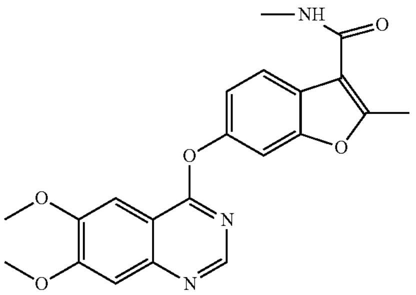

The term "$C_{3-6}$ alkanol" as used herein refers to a fully saturated straight or branched alkyl alcohol, containing 3, 4, 5, or 6 carbon atoms. Examples include but are not limited to, n-propanol, i-propanol, n-butanol, i-butanol, t-butanol, n-pentanol, i-pentanol, n-hexanol, and the like.

The term "$C_{5-8}$ straight or branched alkane" as used herein refers to a fully saturated straight or branched hydrocarbon, containing 5, 6, 7, or 8 carbon atoms. Examples include but are not limited to, n-pentane, n-hexane, n-heptane, n-octane.

The term "organic acid ester with not more than eight carbon atoms" as used herein refers to $R_1COOR_2$, wherein $R_1$ and $R_2$ are independently saturated or unsaturated, straight or branched hydrocarbon radical containing 1, 2, 3, 4, 5, 6, or 7 carbon atoms ($C_{1-17}$ hydrocarbon radical), and the total number of the carbon atoms of $R_1$ and $R_2$ is not more than 7. Examples include but are not limited to, methyl acetate, ethyl acetate, propyl acetate.

The term "haloalkane with less than three carbon atoms" as used herein refers to fully saturated hydrocarbon containing 1 or 2 carbon atoms, which is substituted with one or more halogen atoms selected from F, Cl, Br, or I. Examples include dichloromethane, trichloromethane, carbon tetrachloride, 1,2-dichloroethane, and the like.

The term "about" as used herein refers to the deviation from a given numerical value above or below the given value by a variance of no more than 10%.

The term "substantially free of other forms" as used herein refers to the content of said other forms is less than 40%, preferably less than 30%, preferably less than 20%, preferably less than 10%, preferably less than 5%, preferably less than 1%, by weight.

The term "solution" as used herein means an appropriate mixture for purposes disclosed herein of one or more solutes in one or more solvents. Solution is intended to encompass homogeneous mixtures as well as heterogeneous mixtures, such as slurries or other suspension mixtures having insoluble (not dissolved) material.

The term "organic solvent" as used herein is broadly intended to mean any appropriate organic solvent for purposes disclosed herein.

The term "dissolution solvent" as used herein refers to any organic solvent that is appropriate by being capable of dissolving, in whole or in part, the substrate under suitable conditions, such as an appropriate amount and an appropriate temperature, such as room temperature or an elevated temperature.

The term "anti-dissolution solvent" as used herein refers to any appropriate organic solvent in which the substrate has less solubility than in the dissolution solvent.

"Pharmaceutically acceptable salts" as used herein include, but are not limited to salts with inorganic acids, such as hydrochlorate, hydrobromate, phosphate, phosphite, sulfate, sulfite, nitrate, and like salts; as well as salts with an organic acid, such as malate, maleate, mandelate, fumarate, tartrate, succinate, citrate, aspartate, glutamate, 2-hydroxyl-2-phenylpropionate, gluconate, propionate, lactate, camphorsulfonate, methanesulfonate, ethanesulfonate, naphthalenesulfonate, p-toluenesulfonate, 2-hydroxyethylsulfonate, β-hydroxybutyrate, benzoate, salicylate, stearate, and alkanoate such as acetate, HOOC—(CH2)n-COOH wherein n is 0-4, and like salts. Similarly, pharmaceutically acceptable cations include, but are not limited to, sodium, potassium, calcium, aluminum, lithium, and ammonium.

In addition, if a compound described herein is obtained as an acid addition salt, the free base can be obtained by basifying a solution of the acid addition salt. Conversely, if the product is a free base, an addition salt described above may be produced by dissolving the free base in a suitable organic solvent and treating the solution with an acid, in accordance with conventional procedures for preparing acid addition salts from base compounds. Those skilled in the art will recognize various synthetic methodologies that may be used within the realm of routine experimentation to prepare non-toxic pharmaceutically acceptable addition salts.

The term "effective amount" of the compound of Formula A, including the crystalline form, solvates and the crystalline forms thereof described herein means an amount effective, when administered to a subject in recognized need, such as a human or non-human patient, to alleviate, improve the symptoms, or stop or delay the progression of at least one disease associated with KDR, such as angiogenesis-related disorders, for example cancer, age-related macular degeneration and chronic inflammory disease. "Effective amount" may vary with various factors, such as compound, state of treated disease, severity of treated disease, age and health status of the individual, administration route and form, judgement of the attending physician or a veterinary practitioner, and so on.

The term "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

DETAILED DESCRIPTION OF THE INVENTION

Provided herein are novel crystalline forms, solvates and the crystalline forms thereof of compound 6-((6,7-dimethoxyquinazolin-4-yl)oxy)-N,2-dimethylbenzofuran-3-carboxamide.

The novel crystalline forms of the present invention are crystalline, non-hygroscopic and stable.

As described herein, the novel crystalline forms of the present invention may be identified by any one or more solid state analytical methods. For example, crystalline forms described herein may be characterized according to any one or more of, e.g., X-ray powder diffraction, lattice parameters obtained from a single crystal, Fourier Transform Infrared Spectroscopy, differential scanning calorimetry curve data, and/or a thermogravimetric curve. And if characterization by one of those methods is consistent with the existence of forms described herein, it does not mean that any one of the other methods is inconsistent with that existence.

As described herein, the novel crystalline forms may be characterized according to X-ray powder diffraction. However, it is known in the art that the intensity and/or measured peaks in the X-ray powder diffractogram of different batches of a crystalline form may vary, because of, for example, different experimental conditions and/or preferred orientations. And according to the instrument precision, the measurement error of 26 value is at about ±0.2 2θ. However, known is the value of the relative intensity of the peaks more dependent than peak position on certain properties of the measured samples, such as crystal size in the sample, orientation effect of crystalline and purity of the analysed materials, therefore, the deviation of the peak intensity at about ±20% or greater range may occur. But notwithstanding experimental and machine errors, and principles such as preferred orientation, one skilled in the art can find sufficient information in the XRPD data provided herein to identify Form I and any other crystalline forms described herein.

Form I

Provided herein is Form I of the compound of Formula A.

In some embodiments, Form I of the compound of Formula A may be characterized according to X-ray powder diffraction.

In some embodiments, the X-ray powder diffractogram of the Form I of the compound of Formula A may have characteristic diffraction angles (2θ) of 5.3 degrees, 10.7 degrees, 13.9 degrees, 14.6 degrees, each of the diffraction angles having an error of about ±0.2 degrees (2θ).

In some embodiments, the X-ray powder diffractogram of the Form I of the compound of Formula A may have characteristic diffraction angles (2θ) of 5.3 degrees, 7.3 degrees, 10.7 degrees, 13.9 degrees, 14.6 degrees, 19.9 degrees, each of the diffraction angles having an error of about ±0.2 degrees (2θ).

In some embodiments, the X-ray powder diffractogram of the Form I of the compound of Formula A may have characteristic diffraction angles (2θ) of 5.3 degrees, 7.3 degrees, 10.7 degrees, 13.9 degrees, 14.6 degrees, 16.3 degrees, 19.9 degrees, each of the diffraction angles having an error of about ±0.2 degrees (2θ).

In some embodiments, the X-ray powder diffractogram of the Form I of the compound of Formula A may have characteristic diffraction angles (2θ) of 5.3 degrees, 7.3 degrees, 10.7 degrees, 13.9 degrees, 14.6 degrees, 16.3 degrees, 19.9 degrees, 21.1 degrees, 21.3 degrees, and 25.8 degrees, each of the diffraction angles having an error of about ±0.2 degrees (2θ).

In some embodiments, the X-ray powder diffractogram of the Form I of the compound of Formula A may have characteristic diffraction angles (2θ) of 5.3 degrees, 7.3 degrees, 10.7 degrees, 13.9 degrees, 14.6 degrees, 15.2 degrees, 16.3 degrees, 19.9 degrees, 21.1 degrees, 21.3 degrees, 23.1 degrees, 23.3 degrees, and 25.8 degrees, each of the diffraction angles having an error of about ±0.2 degrees (2θ).

In some embodiments, the Form I of the compound of Formula A may have an X-ray powder diffractogram as shown in FIG. 1. But notwithstanding experimental and machine errors, and principles such as preferred orientation, one skilled in the art can find sufficient information in the XRPD data provided herein to identify Form I of the compound of Formula A and any other crystalline forms.

In some embodiments, Form I of the compound of Formula A may be characterized according to a DSC thermogram. In some embodiments, the Form I of the compound of Formula A has a DSC curve as shown in FIG. 2. In the DSC thermogram, the endothermic peak of the Form I of the compound of Formula A is at about 247.3-248.3° C.

In some embodiments, Form I of the compound of Formula A may be characterized by thermogravimetric analysis (TGA). In some embodiments, the Form I of the compound of Formula A has a TGA curve as shown in FIG. 3 indicating the Form I as described herein as an anhydrous material or a neat form.

In some embodiments, Form I of the compound of Formula A is substantially free of other crystalline Forms as described herein. For example, the content of Form I of the compound of Formula A is at least 99%, at least 95%, at least 90%, or even lower to 80%, by weight. Further for example, the content of Form I of the compound of Formula A is at least 70%, or at least 60%, by weight. Even further for example, the content of Form I of the compound of Formula A is at least 50% by weight.

Methods of Preparing Form I

Method A

Also provided herein is a method of preparing Form I of the compound of Formula A, comprising:

(1) mixing compound 6-((6,7-dimethoxyquinazolin-4-yl)oxy)-N,2-dimethylbenzofuran-3-carboxamide with at least one dissolution solvent or dissolution solvent mixture, and heating the mixture to reflux to obtain a solution;

wherein, said at least one dissolution solvent is selected from methanol, $C_{3-6}$ alkanol, acetic acid, and aprotic solvent; said dissolution solvent mixture is selected from a mixture of two or more aprotic solvents, or a mixture of water miscible organic solvent and water, in which the volume percentage of the water miscible organic solvent in said dissolution solvent mixture is less than about 50%;

(2) cooling the solution obtained in step (1) to ambient temperature slowly; then (3) isolating to obtain the solid of Form I of the compound of Formula A;

(4) drying the solid obtained in step (3).

In some embodiments, said $C_{3-6}$ alkanol is, such as n-propanol, i-propanol, n-butanol, i-butanol, s-butanol, t-butanol, n-pentanol, n-hexanol, and the like.

In some embodiments, said aprotic solvents are selected from acetone, methyl ethyl ketone, toluene, acetonitrile, N,N-dimethylformamide(DMF), tetrahydrofuran(THF), dichloromethane(DCM), and $C_{5-8}$ straight or branched alkane, such as n-heptane.

In some embodiments, said water miscible organic solvent is selected from acetone, methanol, ethanol, and acetonitrile.

In some embodiments, the volume percentage of said water miscible organic solvent in said dissolution solvent mixture is less than about 35%.

In some embodiments, said water miscible organic solvent and water are mixed in proper ratio. In some embodiments, the volume ratio of the water miscible organic solvent and water is about 1:2, such as methanol/water (about 1/2 in V/V), ethanol/water(about 1/2 in V/V), acetonitrile/water(about 1/2 in V/V).

In some embodiments, said at least one dissolution solvent is selected from mixtures of two or three organic solvents, for example, mixtures of acetone and THF (in volume ratio from about 5/1 to about 1/7), mixtures of THF and acetonitrile (in volume ratio from about 1/3 to about 1/7), mixtures of DCM, acetic acid and n-heptane (about 4/1/5 in V/V/V), and the like.

In some embodiments, said cooling the solution to ambient temperature, can cool slowly while stirring, such as stirring at a moderate rate, for example at a rate ranging from 50 to 200 rpm.

In some embodiments, said drying temperature and drying time should be proper to ensure the solid be dried completely and keep the essential properties.

Method B

Also provided herein is an alternative method of preparing Form I of the compound of Formula A, comprising:

(1) mixing compound 6-((6,7-dimethoxyquinazolin-4-yl)oxy)-N,2-dimethylbenzofuran-3-carboxamide with at least one dissolution solvent, then heating the mixture to reflux to obtain the first solution; wherein said dissolution solvent is selected from ethanol, isopropanol, acetone, dichloromethane, dimethyl sulfoxide (DMSO), and N,N-dimethylformamide;

(2) adding at least one anti-dissolution solvent to said first solution to obtain the second solution;

(3) leaving said second solution to cool spontaneously slowly to ambient temperature; then (4) isolating to obtain the solid of Form I of 6-((6,7-dimethoxyquinazolin-4-yl)oxy)-N,2-dimethylbenzofuran-3-carboxamide;

(5) drying the solid obtained in step (4).

In some embodiments, said anti-dissolution solvent is selected from water, $C_{5-8}$ straight or branched alkane (such as n-heptane), and organic acid esters with not more than eight carbon atoms (such as ethyl acetate).

In some embodiments, said anti-dissolution solvent is selected from water, n-heptane, and ethyl acetate.

In some embodiments, the volume ratio of said dissolution solvent to the anti-dissolution solvent ranges from about 0.5:1 to about 2.5:1.

In some embodiments, the amount of said at least one dissolution solvent used in step (1) of method B is about 20 to 380 mL/1 g the compound of Formula A (a volume/weight ratio).

Method C

Also provided herein is an alternative method of preparing Form I of the compound of Formula A, comprising:

(1) suspending the solid of compound 6-((6,7-dimethoxyquinazolin-4-yl)oxy)-N,2-dimethylbenzofuran-3-carboxamide in an appropriate amount of a solvent system; wherein, said solvent system is selected from dissolution solvent (such as acetone), or a solvent mixture of water miscible organic solvent and water, in which volume percentage of water miscible organic solvent in the solvent mixture is less than about 80%;

(2) stirring the suspension obtained in step (1) for a period of time;

(3) isolating to obtain the solid of Form I of 6-((6,7-dimethoxyquinazolin-4-yl)oxy)-N,2-dimethylbenzofuran-3-carboxamide;

(4) drying the solid obtained in step (3).

In some embodiments, said solid of compound 6-((6,7-dimethoxyquinazolin-4-yl)oxy)-N,2-dimethylbenzofuran-3-carboxamide used in step (1) may be a single crystal form, such as Form I, Form II or Form III, or a mixture of two or more of these forms.

In some embodiments, in said step (1), the compound 6-((6,7-dimethoxyquinazolin-4-yl)oxy)-N,2-dimethylbenzofuran-3-carboxamide is not dissolved completely in the suspension system, wherein some remains as solid.

In some embodiments, said water miscible organic solvent is selected from acetone, methanol, ethanol, and acetonitrile. When the selected water miscible organic solvent is ethanol, the volume percentage of ethanol in the solvent system is not more than about 25%.

In some embodiments, said water miscible organic solvent and water are mixed in proper ratio. In some embodiments, the volume ratio of the water miscible organic solvent and water is from about 1:3 to about 1:9, or is about 1:1, such as ethanol/water (about 1/3 to about 1/9 in V/V), acetone/water (about 1/1 in V/V).

In some embodiments, heating is applied in said step (2) when stirring the suspension, and the heating temperature is not higher than the boiling point of the solvent system, such as about 40° C., about 60° C., and about 70° C. Said heating can facilitate the conversion of the solid in the suspension system to Form I of the compound of Formula A.

Ethanol Solvate

Also provided herein is ethanol solvate of the compound of Formula A.

In some embodiments, ethanol solvate of the compound of Formula A is hemiethanol solvate.

In some embodiments, hemiethanol solvate of the compound of Formula A is Form II.

In some embodiments, Form II of hemiethanol solvate of the compound of Formula A may be characterized according to X-ray powder diffraction.

In some embodiments, the X-ray powder diffractogram of Form II of hemiethanol solvate of the compound of Formula A may have characteristic diffraction angles (2θ) of 8.2 degrees, 10.3 degrees, 12.1 degrees, and 13.2 degrees, each of the diffraction angles having an error of about ±0.2 degrees (2θ).

In some embodiments, the X-ray powder diffractogram of Form II of hemiethanol solvate of the compound of Formula A may have characteristic diffraction angles (2θ) of 4.2 degrees, 4.6 degrees, 8.2 degrees, 9.3 degrees, 10.3 degrees, 12.1 degrees, 13.2 degrees, and 14.6 degrees, each of the diffraction angles having an error of about ±0.2 degrees (2θ).

In some embodiments, the X-ray powder diffractogram of Form II of hemiethanol solvate of the compound of Formula A may have characteristic diffraction angles (2θ) of 4.2 degrees, 4.6 degrees, 7.2 degrees, 8.2 degrees, 9.3 degrees, 10.3 degrees, 12.1 degrees, 13.2 degrees, 14.6 degrees, and 18.2 degrees, each of the diffraction angles having an error of about ±0.2 degrees (2θ).

In some embodiments, the X-ray powder diffractogram of Form II of hemiethanol solvate of the compound of Formula A may have characteristic diffraction angles (2θ) of 4.2 degrees, 4.6 degrees, 5.2 degrees, 7.2 degrees, 8.2 degrees, 9.3 degrees, 10.3 degrees, 12.1 degrees, 13.2 degrees, 14.6 degrees, 18.2 degrees, and 23.5 degrees, each of the diffraction angles having an error of about ±0.2 degrees (2θ).

In some embodiments, the X-ray powder diffractogram of Form II of hemiethanol solvate of the compound of Formula A may have characteristic diffraction angles (2θ) of 4.2 degrees, 4.6 degrees, 5.2 degrees, 7.2 degrees, 8.2 degrees, 8.9 degrees, 9.3 degrees, 10.3 degrees, 11.4 degrees, 12.1 degrees, 13.2 degrees, 14.6 degrees, 18.2 degrees, 18.9 degrees, 20.4 degrees, 22.1 degrees, 23.5 degrees, and 26.2 degrees, each of the diffraction angles having an error of about ±0.2 degrees (2θ).

In some embodiments, the Form II of hemiethanol solvate of the compound of Formula A may have an X-ray powder diffractogram as shown in FIG. 4. But notwithstanding experimental and machine errors, and principles such as preferred orientation, one skilled in the art can find sufficient information in the XRPD data provided herein to identify Form II of hemiethanol solvate of the compound of Formula A and any other crystalline forms.

In some embodiments, Form II of hemiethanol solvate of the compound of Formula A may be characterized according to a DSC thermogram. In some embodiments, the Form II of hemiethanol solvate of the compound of Formula A has a DSC curve as shown in FIG. 5. In the DSC thermogram, the endothermic peak of the Form II of hemiethanol solvate of the compound of Formula A is at about 245.7-247.0° C.

In some embodiments, Form II of hemiethanol solvate of the compound of Formula A may be characterized by thermogravimetric analysis (TGA). In some embodiments, the Form II of hemiethanol solvate of the compound of Formula A has a TGA curve as shown in FIG. 6 indicating the Form II as described herein as a hemiethanol solvate.

In some embodiments, Form II of hemiethanol solvate of the compound of Formula A is substantially free of other crystalline Forms as described herein. For example, the content of Form II of hemiethanol solvate of the compound of Formula A is at least 99%, at least 95%, at least 90%, or even lower to 80%, by weight. Further for example, the content of Form II of hemiethanol solvate of the compound of Formula A is at least 70%, or at least 60%, by weight. Even further for example, the content of Form II of hemiethanol solvate of the compound of Formula A is at least 50% by weight.

Method of Preparing Form II

Method A

Also provided herein is a method of preparing Form II of hemiethanol solvate of the compound of Formula A, comprising:

(1) mixing compound 6-((6,7-dimethoxyquinazolin-4-yl)oxy)-N,2-dimethylbenzofuran-3-carboxamide with at least one dissolution solvent, and heating the mixture to reflux to obtain a solution;
   wherein, said dissolution solvent is selected from ethanol, or a solvent mixture of ethanol and an aprotic solvent, in which volume percentage of ethanol in the solvent mixture is not less than about 65%;

(2) cooling the solution obtained in step (1) to ambient temperature slowly; then (3) isolating to obtain the solid of Form II of 6-((6,7-dimethoxyquinazolin-4-yl)oxy)-N,2-dimethylbenzofuran-3-carboxamide;

(4) drying the solid obtained in step (3).

In some embodiments, said aprotic solvent is tetrahydrofuran or water. In some embodiments, said ethanol and aprotic solvent are mixed in proper ratio to form the solvent mixture. In some embodiments, the volume ratio of ethanol and aprotic solvent is about 5:1 or about 2:1, such as ethanol/tetrahydrofuran (about 5/1 in V/V), ethanol/water (about 2/1 in V/V).

In some embodiments, said cooling the solution to ambient temperature, can cool slowly while stirring, such as stirring at a moderate rate, for example at a rate ranging from 50 to 200 rpm.

In some embodiments, proper drying temperature and drying time is required to ensure the solid be dried completely and keep the wanted crystal form properties.

Method B

Also provided herein is an alternative method of preparing Form II of hemiethanol solvate of the compound of Formula A, comprising:

(1) mixing compound 6-((6,7-dimethoxyquinazolin-4-yl)oxy)-N,2-dimethylbenzofuran-3-carboxamide with at least one dissolution solvent, then heating the mixture to reflux to obtain the first solution;
   wherein, said dissolution solvent is selected from ethanol, or a solvent mixture of ethanol and a weak organic acid;

(2) adding at least one anti-dissolution solvent to said first solution at refluxing temperature to obtain the second solution, wherein said anti-dissolution solvent is $C_{5-8}$ straight or branched alkane, such as n-heptane;

(3) leaving said second solution to cool spontaneously slowly to ambient temperature; then (4) isolating to obtain the solid of Form II of 6-((6,7-dimethoxyquinazolin-4-yl)oxy)-N,2-dimethylbenzofuran-3-carboxamide;

(5) drying the solid obtained in step (4).

In some embodiments, said weak organic acid is acetic acid. In some more specific embodiments, the volume ratio of ethanol and acetic acid is about 1:3.

In some embodiments, the volume percentage of ethanol in the solvent system (total amount of the dissolution solvent and the anti-dissolution solvent) is not less than about 30%.

In some embodiments, the amount of said dissolution solvent system consisting of ethanol and a weak organic acid is 60 to 300 mL/1 g Compound A used in step (1) (a volume/weight ratio).

Method C

Also provided herein is an alternative method of preparing Form II of hemiethanol solvate of the compound of Formula A, comprising:

(1) suspending the solid of compound 6-((6,7-dimethoxyquinazolin-4-yl)oxy)-N,2-dimethylbenzofuran-3-carboxamide in an appropriate amount of a solvent system; wherein, said solvent system is selected from ethanol, a solvent mixture of ethanol and $C_{5-8}$ straight or branched alkane (such as n-heptane), or a solvent mixture of ethanol and water, in which volume percentage of ethanol in the solvent mixture of ethanol and water is not less than about 80%;

(2) stirring the suspension obtained in step (1) for a period of time at certain temperature range;

(3) isolating to obtain the Form II of 6-((6,7-dimethoxyquinazolin-4-yl)oxy)-N,2-dimethylbenzofuran-3-carboxamide.

In some embodiments, said solid of compound 6-((6,7-dimethoxyquinazolin-4-yl)oxy)-N,2-dimethylbenzofuran-3-carboxamide used in step (1) may be a single crystal form, such as Form I, Form II, Form III or Form IV, or a mixture of two or more of these forms.

In some embodiments, the volume ratio of ethanol and $C_{5-8}$ straight or branched alkane (such as n-heptane) in said solvent mixture is about 1:4. In some embodiments, the proper volume ratio of ethanol and water is about 4:1.

As described herein, the stirring is carried out at temperature less than the boiling point of the solvent system, such as at room temperature, about 40° C. and about 60° C.

Form III

Also provided herein is Form III of the compound of Formula A.

In some embodiments, Form III of the compound of Formula A may be characterized according to X-ray powder diffraction.

In some embodiments, the X-ray powder diffractogram of the Form III of the compound of Formula A may have characteristic diffraction angles (2θ) of 7.2 degrees, 8.6 degrees, 14.4 degrees, and 15.2 degrees, each of the diffraction angles having an error of about ±0.2 degrees (2θ).

In some embodiments, the X-ray powder diffractogram of the Form III of the compound of Formula A may have characteristic diffraction angles (2θ) of 4.9 degrees, 7.2 degrees, 8.6 degrees, 12.0 degrees, 14.4 degrees, 15.2 degrees, 25.4 degrees, and 26.1 degrees, each of the diffraction angles having an error of about ±0.2 degrees (2θ).

In some embodiments, the X-ray powder diffractogram of the Form III of the compound of Formula A may have characteristic diffraction angles (2θ) of 4.9 degrees, 7.2 degrees, 8.6 degrees, 12.0 degrees, 14.4 degrees, 15.2 degrees, 25.4 degrees, 26.1 degrees, and 29.1 degrees, each of the diffraction angles having an error of about ±0.2 degrees (2θ).

In some embodiments, the X-ray powder diffractogram of the Form III of the compound of Formula A may have characteristic diffraction angles (2θ) of 4.9 degrees, 7.2 degrees, 8.6 degrees, 12.0 degrees, 14.4 degrees, 15.2 degrees, 16.2 degrees, 20.4 degrees, 22.4 degrees, 25.4 degrees, 26.1 degrees, 29.1 degrees, and 32.7 degrees, each of the diffraction angles having an error of about ±0.2 degrees (2θ).

In some embodiments, the X-ray powder diffractogram of the Form III of the compound of Formula A may have characteristic diffraction angles (2θ) of 4.9 degrees, 7.2 degrees, 8.6 degrees, 12.0 degrees, 14.4 degrees, 15.2 degrees, 16.2 degrees, 17.3 degrees, 19.9 degrees, 20.4 degrees, 22.4 degrees, 24.0 degrees, 24.3 degrees, 24.9 degrees, 25.4 degrees, 26.1 degrees, 29.1 degrees, and 32.7 degrees, each of the diffraction angles having an error of about ±0.2 degrees (2θ).

In some embodiments, the Form III of the compound of Formula A may have an X-ray powder diffractogram as shown in FIG. 7. But notwithstanding experimental and machine errors, and principles such as preferred orientation, one skilled in the art can find sufficient information in the XRPD data provided herein to identify Form III and any other crystalline forms.

In some embodiments, Form III of the compound of Formula A may be characterized according to a DSC thermogram. In some embodiments, the Form III of the compound of Formula A has a DSC curve as shown in FIG. 8. In the DSC thermogram, the endothermic peak of the Form III of the compound of Formula A is at about 248.0-249.0° C.

In some embodiments, Form III of the compound of Formula A may be characterized by thermogravimetric analysis (TGA). In some embodiments, the Form III of the compound of Formula A has a TGA curve as shown in FIG. 9 indicating the Form III as an anhydrous material or a neat form.

In some embodiments, said Form III of the compound of Formula A is substantially free of other crystalline Forms as described herein. For example, the content of Form III is at least 99%, at least 95%, at least 90%, or even lower to 80%, by weight. Further for example, the content of Form III is at least 70%, or at least 60%, by weight. Even further for example, the content of Form III is at least 50% by weight.

Method of Preparing Form III

Also provided herein is a method of preparing Form III of the compound of Formula A, comprising:

(1) mixing compound 6-((6,7-dimethoxyquinazolin-4-yl)oxy)-N,2-dimethylbenzofuran-3-carboxamide with a solvent mixture of an aprotic solvent and water, wherein the volume ratio of said aprotic solvent and water in the solvent mixture is no less than about 1:2.5, and heating the mixture to obtain a solution;

(2) cooling the solution obtained in step (1) to ambient temperature slowly; then (3) isolating to obtain the Form III of 6-((6,7-dimethoxyquinazolin-4-yl)oxy)-N,2-dimethylbenzofuran-3-carboxamide.

In some embodiments, said aprotic solvent is selected from tetrahydrofuran and acetonitrile.

In some embodiments, said aprotic solvent and water are mixed in proper volume ratio to form a dissolution solvent. For example, the volume ratio of said aprotic solvent and water ranges from about 1:1 to about 7:1, such as tetrahydrofuran/water (about 1/1 in V/V to about 3/1 in V/V), acetonitrile/water (about 1/1 in V/V to about 7/1 in V/V).

In some embodiments, in said step (1), heating the mixture to reflux or to such as about 72° C.

Cooling the solution to ambient temperature, as described herein, can be slowly cooled while stirring, such as cooled while stirring at a moderate rate, for example at a rate ranging from 50 to 200 rpm.

Acetic Acid Solvate

Also provided herein is acetic acid solvate of the compound of Formula A.

In some embodiments, acetic acid solvate of the compound of Formula A is monoacetic acid solvate.

In some embodiments, monoacetic acid solvate of the compound of Formula A is Form IV.

In some embodiments, Form IV of monoacetic acid solvate of the compound of Formula A may be characterized according to X-ray powder diffraction.

In some embodiments, the X-ray powder diffractogram of Form IV of monoacetic acid solvate of the compound of Formula A may have characteristic diffraction angles (2θ) of 5.7 degrees, 7.6 degrees, 10.5 degrees, and 11.5 degrees, each of the diffraction angles having an error of about ±0.2 degrees (2θ).

In some embodiments, the X-ray powder diffractogram of the Form IV of monoacetic acid solvate of the compound of Formula A may have characteristic diffraction angles (2θ) of 5.7 degrees, 7.6 degrees, 10.1 degrees, 10.5 degrees, 11.5 degrees, 13.3 degrees, 15.4 degrees, and 17.3 degrees, each of the diffraction angles having an error of about ±0.2 degrees (2θ).

In some embodiments, the X-ray powder diffractogram of the Form IV of monoacetic acid solvate of the compound of Formula A may have characteristic diffraction angles (2θ) of 5.7 degrees, 7.6 degrees, 10.1 degrees, 10.5 degrees, 11.5 degrees, 13.3 degrees, 15.4 degrees, 17.3 degrees, and 20.2 degrees, each of the diffraction angles having an error of about ±0.2 degrees (2θ).

In some embodiments, the X-ray powder diffractogram of the Form IV of monoacetic acid solvate of the compound of Formula A may have characteristic diffraction angles (2θ) of 5.7 degrees, 7.6 degrees, 10.1 degrees, 10.5 degrees, 11.5 degrees, 13.3 degrees, 15.4 degrees, 17.3 degrees, 20.2 degrees, 21.2 degrees, 22.7 degrees, 26.4 degrees, 26.9 degrees, 31.0 degrees, and 32.9 degrees, each of the diffraction angles having an error of about ±0.2 degrees (2θ).

In some embodiments, the X-ray powder diffractogram of the Form IV of monoacetic acid solvate of the compound of Formula A may have characteristic diffraction angles (2θ) of 5.7 degrees, 7.6 degrees, 10.1 degrees, 10.5 degrees, 11.5 degrees, 13.3 degrees, 15.4 degrees, 16.3 degrees, 17.3 degrees, 18.1 degrees, 20.2 degrees, 21.2 degrees, 22.1 degrees, 22.7 degrees, 26.4 degrees, 26.9 degrees, 29.7 degrees, 31.0 degrees, 32.0 degrees, and 32.9 degrees, each of the diffraction angles having an error of about ±0.2 degrees (2θ).

In some embodiments, the Form IV of monoacetic acid solvate of the compound of Formula A may have an X-ray powder diffractogram as shown in FIG. 10. But notwithstanding experimental and machine errors, and principles such as preferred orientation, one skilled in the art can find sufficient information in the XRPD data provided herein to identify Form IV of monoacetic acid solvate of the compound of Formula A and any other crystalline forms.

In some embodiments, Form IV of monoacetic acid solvate of the compound of Formula A may be characterized according to a DSC thermogram. In some embodiments, the Form IV of monoacetic acid solvate of the compound of Formula A has a DSC curve as shown in FIG. 11. In the DSC thermogram, the endothermic peak of the Form IV of monoacetic acid solvate of the compound of Formula A is at about 245.1-247.4° C.

In some embodiments, Form IV of monoacetic acid solvate of the compound of Formula A may be characterized by thermogravimetric analysis (TGA). In some embodiments, the Form IV of monoacetic acid solvate of the compound of Formula A has a TGA curve as shown in FIG. 12 indicating the Form IV as described herein as a monoacetic acid solvate.

In some embodiments, Form IV of monoacetic acid solvate of the compound of Formula A is substantially free of other crystalline Forms as described herein. For example, the content of Form IV of monoacetic acid solvate of the compound of Formula A is at least 99%, at least 95%, at least 90%, or even lower to 80%, by weight. Further for example, the content of Form IV of monoacetic acid solvate of the compound of Formula A is at least 70%, or at least 60%, by weight. Even further for example, the content of Form IV of monoacetic acid solvate of the compound of Formula A is at least 50% by weight.

Method of Preparing Form IV

Also provided herein is a method of preparing Form IV of monoacetic acid solvate of the compound of Formula A, comprising:

(1) mixing compound 6-((6,7-dimethoxyquinazolin-4-yl)oxy)-N,2-dimethylbenzofuran-3-carboxamide with the solvent system containing acetic acid, and heating the mixture to reflux to obtain the first solution;
(2) adding at least one anti-dissolution solvent to the first solution to obtain the second solution;
(3) leaving the second solution to cool spontaneously slowly to ambient temperature; then
(4) isolating to obtain the Form IV of 6-((6,7-dimethoxyquinazolin-4-yl)oxy)-N,2-dimethylbenzofuran-3-carboxamide.

In some embodiments, said solvent system is selected from a solvent mixture of acetic acid and haloalkane with less than three carbon atoms (such as dichloromethane), or acetic acid alone is used as the solvent system. In some more specific embodiments, the percentage of acetic acid in said solvent system is not lower than 5%. In some more specific embodiments, the volume ratio of acetic acid and dichloromethane is about 5:1.

In some embodiments, said anti-dissolution solvent is selected from $C_{5-8}$ straight or branched alkane, such as n-heptane.

In some embodiments, the volume ratio of said anti-dissolution solvent to the solvent system is not less than about 1:1.

In some embodiments, the amount of the solvent system used in step (1) of said method is about 20 to 30 mL/1 g Compound A (a volume/weight ratio).

Form VII

Also provided herein is Form VII of the compound of Formula A.

In some embodiments, Form VII of the compound of Formula A may be characterized according to X-ray powder diffraction.

In some embodiments, the X-ray powder diffractogram of the Form VII of the compound of Formula A may have characteristic diffraction angles (2θ) of 9.0 degrees, 11.8 degrees, and 13.6 degrees, each of the diffraction angles having an error of about ±0.2 degrees (2θ).

In some embodiments, the X-ray powder diffractogram of the Form VII of the compound of Formula A may have characteristic diffraction angles (2θ) of 6.8 degrees, 9.0 degrees, 11.8 degrees, 13.6 degrees, 14.9 degrees, and 18.2 degrees, each of the diffraction angles having an error of about ±0.2 degrees (2θ).

In some embodiments, the X-ray powder diffractogram of the Form VII of the compound of Formula A may have characteristic diffraction angles (2θ) of 5.9 degrees, 6.8 degrees, 7.1 degrees, 9.0 degrees, 11.8 degrees, 13.6 degrees, 14.9 degrees, and 18.2 degrees, each of the diffraction angles having an error of about ±0.2 degrees (2θ).

In some embodiments, the X-ray powder diffractogram of the Form VII of the compound of Formula A may have characteristic diffraction angles (2θ) of 5.9 degrees, 6.8 degrees, 7.1 degrees, 9.0 degrees, 11.8 degrees, 13.6 degrees, 14.9 degrees, 18.2 degrees, 21.4 degrees, 23.7 degrees, and 26.0 degrees, each of the diffraction angles having an error of about ±0.2 degrees (2θ).

In some embodiments, the X-ray powder diffractogram of the Form VII of the compound of Formula A may have characteristic diffraction angles (2θ) of 5.9 degrees, 6.8 degrees, 7.1 degrees, 9.0 degrees, 11.8 degrees, 13.6 degrees, 14.9 degrees, 18.2 degrees, 19.1 degrees, 19.7 degrees, 21.4 degrees, 23.7 degrees, 26.0 degrees, 27.5 degrees, 28.1 degrees, 29.1 degrees, and 30.0 degrees, each of the diffraction angles having an error of about ±0.2 degrees (2θ).

In some embodiments, the Form VII of the compound of Formula A may have an X-ray powder diffractogram as shown in FIG. 13. But notwithstanding experimental and machine errors, and principles such as preferred orientation, one skilled in the art can find sufficient information in the XRPD data provided herein to identify Form VII of the compound of Formula A and any other crystalline forms.

In some embodiments, Form VII of the compound of Formula A may be characterized according to a DSC thermogram. In some embodiments, the Form VII of the compound of Formula A has a DSC curve as shown in FIG. 14. In the DSC thermogram, the endothermic peak of the Form VII of the compound of Formula A is at about 245.4-247.8° C.

In some embodiments, Form VII of the compound of Formula A may be characterized by thermogravimetric analysis (TGA). In some embodiments, the Form VII of the compound of Formula A has a TGA curve as shown in FIG. 15 indicating the Form VII as described herein as an anhydrous material or a neat form.

In some embodiments, Form VII of the compound of Formula A is substantially free of other crystalline Forms as described herein. For example, the content of Form VII of the compound of Formula A is at least 99%, at least 95%, at least 90%, or even lower to 80%, by weight. Further for example, the content of Form VII of the compound of Formula A is at least 70%, or at least 60%, by weight. Even further for example, the content of Form VII of the compound of Formula A is at least 50% by weight.

Method of Preparing Form VII

Also provided herein is a method of preparing Form VII of the compound of Formula A, comprising:

(1) mixing compound 6-((6,7-dimethoxyquinazolin-4-yl)oxy)-N,2-dimethylbenzofuran-3-carboxamide with solvent mixture of an aprotic solvent and water, wherein the volume ratio of said aprotic solvent and water in the solvent mixture is about 1:1, and heating the mixture to reflux to obtain a solution;

(2) cooling the solution obtained in step (1) to ambient temperature slowly; then (3) isolating the solid precipitates obtained in step (2);

(4) drying the solid to get the Form VII of 6-((6,7-dimethoxyquinazolin-4-yl)oxy)-N,2-dimethylbenzofuran-3-carboxamide.

In some embodiments, said aprotic solvent is selected from tetrahydrofuran.

In some embodiments, said cooling the solution to ambient temperature, can be slowly cooled while stirring, such as cooled while stirring at a moderate rate, for example at a rate ranging from 50 to 200 rpm.

In some embodiments, the drying conditions in step (4) are selected from ambient pressure to vacuums, and temperature from room temperature to about 55° C., and drying time from about 16 hours to about 48 hours.

Dioxane Solvate

Also provided herein is dioxane solvate of the compound of Formula A.

In some embodiments, dioxane solvate of the compound of Formula A is monodioxane solvate.

In some embodiments, monodioxane solvate of the compound of Formula A is Form VIII.

In some embodiments, Form VIII of monodioxane solvate of the compound of Formula A may be characterized according to X-ray powder diffraction.

In some embodiments, the X-ray powder diffractogram of Form VIII of monodioxane solvate of the compound of Formula A may have characteristic diffraction angles (2θ) of 9.0 degrees, 14.5 degrees, 16.3 degrees, and 16.8 degrees, each of the diffraction angles having an error of about ±0.2 degrees (2θ).

In some embodiments, the X-ray powder diffractogram of the Form VIII of monodioxane solvate of the compound of Formula A may have characteristic diffraction angles (2θ) of 5.7 degrees, 8.2 degrees, 9.0 degrees, 11.4 degrees, 14.5 degrees, 16.3 degrees, and 16.8 degrees, each of the diffraction angles having an error of about ±0.2 degrees (2θ).

In some embodiments, the X-ray powder diffractogram of the Form VIII of monodioxane solvate of the compound of Formula A may have characteristic diffraction angles (2θ) of 5.7 degrees, 8.2 degrees, 9.0 degrees, 11.4 degrees, 12.7 degrees, 14.5 degrees, 16.3 degrees, 16.8 degrees, 22.9 degrees, and 25.9 degrees, each of the diffraction angles having an error of about ±0.2 degrees (2θ).

In some embodiments, the X-ray powder diffractogram of the Form VIII of monodioxane solvate of the compound of Formula A may have characteristic diffraction angles (2θ) of 5.7 degrees, 8.2 degrees, 9.0 degrees, 11.4 degrees, 12.7 degrees, 14.5 degrees, 16.3 degrees, 16.8 degrees, 17.9 degrees, 22.9 degrees, 25.9 degrees, and 29.8 degrees, each of the diffraction angles having an error of about ±0.2 degrees (2θ).

In some embodiments, the X-ray powder diffractogram of the Form VIII of monodioxane solvate of the compound of Formula A may have characteristic diffraction angles (2θ) of 5.7 degrees, 8.2 degrees, 9.0 degrees, 11.4 degrees, 12.7 degrees, 14.5 degrees, 16.3 degrees, 16.8 degrees, 17.9 degrees, 20.3 degrees, 21.6 degrees, 21.9 degrees, 22.9 degrees, 23.7 degrees, 24.5 degrees, 25.9 degrees, 29.2 degrees, 29.8 degrees, 33.9 degrees, and 37.4 degrees, each of the diffraction angles having an error of about ±0.2 degrees (2θ).

In some embodiments, the Form VIII of monodioxane solvate of the compound of Formula A may have an X-ray powder diffractogram as shown in FIG. 16. But notwithstanding experimental and machine errors, and principles such as preferred orientation, one skilled in the art can find sufficient information in the XRPD data provided herein to identify Form VIII of monodioxane solvate of the compound of Formula A and any other crystalline forms.

In some embodiments, Form VIII of monodioxane solvate of the compound of Formula A may be characterized according to a DSC thermogram. In some embodiments, the Form VIII of monodioxane solvate of the compound of Formula A has a DSC curve as shown in FIG. 17. In the DSC thermogram, the endothermic peak of the Form VIII of monodioxane solvate of the compound of Formula A is at about 245.6-248.3° C.

In some embodiments, Form VIII of monodioxane solvate of the compound of Formula A may be characterized by thermogravimetric analysis (TGA). In some embodiments, the Form VIII of monodioxane solvate of the compound of Formula A has a TGA curve as shown in FIG. 18 indicating the Form VIII as described herein as a monodioxane solvate.

In some embodiments, Form VIII of monodioxane solvate of the compound of Formula A is substantially free of other crystalline Forms as described herein. For example, the content of Form VIII of monodioxane solvate of the compound of Formula A is at least 99%, at least 95%, at least 90%, or even lower to 80%, by weight. Further for example, the content of Form VIII of monodioxane solvate of the compound of Formula A is at least 70%, or at least 60%, by weight. Even further for example, the content of Form VIII of monodioxane solvate of the compound of Formula A is at least 50% by weight.

Method of Preparing Form VIII

Also provided herein is a method of preparing Form VIII of monodioxane solvate of the compound of Formula A, comprising:

(1) mixing compound 6-((6,7-dimethoxyquinazolin-4-yl)oxy)-N,2-dimethylbenzofuran-3-carboxamide with dioxane, and heating the mixture to reflux to obtain a solution;

(2) cooling the solution obtained in step (1) to ambient temperature slowly; then (3) isolating to obtain the Form VIII of 6-((6,7-dimethoxyquinazolin-4-yl)oxy)-N,2-dimethylbenzofuran-3-carboxamide.

In some embodiments, the amount of dioxane used in said step (1) is not less than about 80 mL/1 g the compound of Formula A (a volume/weight ratio).

The features of each embodiment in above methods of preparing the crystalline forms of the compound of Formula A or its solvates can be arbitrary combined, each embodiment obtained from such mutual combinations is included within the scope of the present invention, as these embodiments obtained from such mutual combinations are specifically and individually listed herein.

Pharmaceutical Compositions and Methods of Treatment

The crystalline forms of the compound of Formula A, its solvates and the crystalline forms thereof (such as Form I, Form II, Form III, Form IV, Form VII, and Form VIII) may be used for the treatment of diseases mediated by KDR, such as angiogenesis-related disorders.

For example, the angiogenesis-related disorders include age-related vascular degenerative disease, such as age-related macular degeneration, cancer, and chronic inflammory disease. Cancers as described herein include but are not limited to lung cancer, head and neck cancer, colorectal cancer, pancreatic cancer, colon cancer, breast cancer, ovarian cancer, prostate cancer, stomach cancer, kidney cancer, liver cancer, brain cancer, bone cancer, sarcoma, such as soft tissue sarcoma, and leukemia.

Provided herein is the method of treating diseases associated with KDR, such as angiogenesis-related disorders, comprises administering the active pharmaceutical ingredients formed by the compound of Formula A, or pharmaceutically acceptable salts thereof, or one or more crystalline forms of the compound of Formula A and/or its solvates or the crystalline forms thereof, such as Form I, Form II, Form III, Form IV, Form VII, or Form VIII.

In some embodiments, the treatment method is against at least one disease associated with KDR, such as angiogenesis-related disorders, for example cancer. Wherein, a subject in recognized need of treatment is administered an effective amount of a pharmaceutical composition comprising: at least one pharmaceutically acceptable carrier and one or more of the crystalline forms of compound of Formula A, solvates of the compound of Formula A and the crystalline forms thereof (such as Form I, Form II, Form III, Form IV, Form VII, or Form VIII), to provide said treatment.

The amount of the at least one active pharmaceutical ingredient selected from the compound of Formula A and/or pharmaceutically acceptable salts thereof, or the crystalline forms of the compound of Formula A, or the solvates of the compound of Formula A or the crystalline forms thereof (such as Form I, Form II, Form III, Form IV, Form VII, or Form VIII) effective for achieving the desired biological effect may depend on a number of factors, for example, the intended use, the mode of administration, and the clinical condition of the patient. The daily dose may, for example, range from 0.01 mg to 3 g/day (such as from 0.05 mg to 2 g/day, for example from 100 mg to 1 g/day). Unit dose formulations which can be administered orally include, for example, tablets or capsules.

For the therapy of the above-mentioned conditions, the at least one active pharmaceutical ingredient selected from the crystalline forms of the compound of Formula A, the solvates of the compound of Formula A and the crystalline forms thereof may be administered in form of the compound itself, but typically each of them would be used in the form of a pharmaceutical composition with one or more pharmaceutically acceptable carriers/excipients.

Representative carriers/excipients should be compatible with the other ingredients of the composition and not harmful for the patient's health. The carrier/excipient may be a solid or a liquid or both, and may be formulated with the crystalline forms of the compound of Formula A and/or the solvates of the compound of Formula A or the crystalline forms thereof (such as Form I, Form II, Form III, Form IV, Form VII, and/or Form VIII), to a pharmaceutical composition or a unit dosage form (for example, a tablet, a capsule), which may contain from 0.05% to 95% by weight of the compound of Formula A described herein. The pharmaceutical compositions described herein can be produced by known pharmaceutical methods, such as those involving mixing the ingredients with pharmaceutically acceptable carriers and/or excipients and diluents.

In some embodiments, representative carriers or excipients would include but are not limited to: microcrystalline cellulose, lactose, sodium citrate, calcium carbonate, dicalcium phosphate, glycine, disintegrants such as starch, sodium cross-linked carboxymethyl cellulose, composite silicates, and polyethylene glycol with high molecular weight, granulation binders (such as polyvinylpyrrolidone, sucrose, gelatin, and Gum Arabic), and lubricants (such as magnesium stearate, glycerin, and talc).

In some embodiments, the at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII) may be combined with at least one component, such as carrier and/or excipient and/or diluent, selected from sweeteners, flavoring agents, coloring agents, dyes, and emulsifiers.

In some embodiments, the conversion of the crystalline forms of the compound of Formula A, the solvates of the compound of Formula A and the crystalline forms thereof (such as Form I, Form II, Form III, Form IV, Form VII, and Form VIII) will not occur upon formulation with the one or more pharmaceutically acceptable carriers and/or excipients and/or diluents. In other embodiments, the crystalline forms of the compound of Formula A, or the solvates of the compound of Formula A or the crystalline forms thereof (such as Form I, Form II, Form III, Form IV, Form VII, or Form VIII) may be converted, in whole or in part, to one or more other forms, including a non-solid form, upon formulation with the one or more pharmaceutically acceptable carriers and/or diluents and/or excipients. Exemplary carriers and/or diluents and/or excipients would include but are not limited to, water, ethanol, propylene glycol, glycerine, and mixtures thereof. In some embodiments, the Form I or other forms described herein can be dissolved when formulated into a pharmaceutical composition. Accordingly, in such "dissolved" cases, the Form I or other forms no longer exists in their respective crystalline forms in the pharmaceutical composition.

In some embodiments, the at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII) is formulated to a suitable dosage form.

Pharmaceutical compositions described herein can be dosage forms suitable for oral and oral cavity (for example sublingual) administration, although the suitable mode of administration may depend in each individual case on the nature and severity of the condition to be treated and on the nature of the active pharmaceutical ingredient selected from the crystalline forms of the compound of Formula A, the solvates of the compound of Formula A and the crystalline forms thereof (such as Form I, Form II, Form III, Form IV, Form VII, and Form VIII) used in each case to prepare the pharmaceutical composition. Pharmaceutical compositions described herein can be coated dosage forms or coated sustained-release dosage forms. Acid- and gastric juice-resistant dosage forms are also possible. Suitable coatings resistant to gastric juice comprise cellulose acetate phthalate, polyvinyl acetate phthalate, hydroxypropylmethylcellulose phthalate, anionic polymers of methacrylic acid, and methyl methacrylate.

Suitable pharmaceutical compositions for oral administration prepared from the at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII) may be in the form of unit dosage forms such as capsules, cachets, and tablets, including suckable tablets, each of which is prepared with a defined amount of the at least one active pharmaceutical ingredient described herein; as well as in the forms selected from powders, granules, solutions, suspensions in an aqueous or nonaqueous liquid, and oil-in-water and water-in-oil emulsions. Those compositions may, as already mentioned, be prepared by any suitable pharmaceutical formulation methods, such as those including a step wherein the at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII) and a carrier and/or excipient and/or diluent (which may consist of one or more added ingredients) are brought into contact. The compositions can generally be produced by uniformly and homogeneously mixing the at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII) with liquid or finely divided solid carriers, after which the product can be shaped.

The compositions disclosed herein can be administered topically or systemically.

Pharmaceutical compositions which are suitable for peroral (including sublingual) administration can comprise suckable tablets which comprise the at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII), and a flavoring agent. The flavoring agent is selected from sucrose, gum arabic, tragacanth, and the like.

Pharmaceutical compositions described herein can also be those forms suitable for parenterally administration, such as by inhalation spray, or via an implanted reservoir. Solid carriers used therein include, for example, starch, lactose, microcrystalline cellulose, aluminum silicate, and any ingredients suitable for intend use. Liquid carriers include, for example, injectable water, polyvinyl alcohol, non-ionized surfactant agents, and corn oil, and any ingredients suitable for intend use. Other excipients commonly used in pharmaceutical formulation include coloring agents, preservatives, flavoring agents and antioxidants such as vitamin E, vitamin A, BHT and BHA.

The crystalline forms of the compound of Formula A, the solvates of the compound of Formula A and the crystalline forms thereof described herein, can also be administered intraperitoneally. And the solution and suspension of those compounds can be prepared by dissolving or suspending the compound in water containing suitable surfactants. Dispersed suspensions can be prepared by using glycerol, polyethylene glycol (PEG) or their mixture with suitable oils. Preservatives can be added to those formulations to prevent growth of microorganisms during use.

Injectable formulation includes solution or suspension in sterilized water, and sterilized powder. In all cases, those formulations must be sterilized and easily removed from the syringe, and stable under the manufacture and storage conditions, and free from pollution and the infection of microorganisms. Carriers can be solvents or dispersing agents, and include water, alcohol, and some suitable oils.

The at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII) can also be administered in combination with one or more other active ingredients (such as in the synergetic therapy). When administered as a combination, the active ingredients can be formulated as separate compositions that are administered at the same time or sequentially at different times (such as administered sequentially in any orders) through the same or different administration routes, or the active ingredients can be administered in the same pharmaceutical composition.

In some embodiments, the at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII) can be administered in combination with one or more other active ingredients with known therapeutical effect, for example for the treatment of diseases associated with KDR, such as angiogenesis-related disorders.

The phrase "in combination with", as used herein, defines the combined use of the at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII) with one or more other active ingredients, such as, the combined use in the anti-neoplastic method. As used herein, the term "anti-neoplastic method" refers to any method for purposes of treating the cancer. Examples of anti-neoplastic method include but are not limited to: radiotherapy, immunotherapy, DNA damaging chemotherapy, and chemotherapy that disrupts cell replication.

Non-limiting examples of DNA damaging chemotherapeutic agents include, for example, topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include but are not limited to: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-kappa B inhibitors, including inhibitors of I kappa B kinase; antibodies which bind to proteins overexpressed in cancers and thereby downregulate cell replication (e.g., rituximab, cetuximab, and bevacizumab); and other inhibitors of proteins or enzymes known to be upregulated, over-expressed, or activated in cancers, the inhibition of which can downregulates cell replication.

Thus, methods described herein are not limited in the sequence of administration; the at least one active pharmaceutical ingredient selected from the crystalline forms of the compound of Formula A, the solvates of the compound of Formula A and the crystalline forms thereof (such as Form I, Form II, Form III, Form IV, Form VII, and Form VIII) may be administered either prior to, at the same time with or after administration of the one or more other active ingredients. At least one active pharmaceutical ingredient in the combination described above is selected from the crystalline forms of the compound of Formula A, the solvates of the compound of Formula A and the crystalline forms thereof (such as Form I, Form II, Form III, Form IV, Form VII, and Form VIII)

The following non-limiting examples are provided.

EXPERIMENTS

The compound of Formula A material used in the examples are prepared according to WO 2009/137797 A2.

All reagents, except intermediates, used in this disclosure are commercially available. All compound names except the reagents were generated by ChemBioDraw Ultra 12.0.

Unless otherwise indicated, powder X-ray diffractograms were obtained using Germany Bruker D8 ADVANCE X-ray diffractometer, with radiation generated from a CuKa source at 40 mA and 40 kV, and the instrument can be operated over the 2θ range of 3-45° with scan step of 0.02° and scanning speed at 4°/min.

DSC thermal analyses were performed on PerkinElmer DSC 7, in which nitrogen was used as the purge gas at a flow rate of 50 mL $min^{-1}$. The samples were measured in crimped aluminum pans. The instruments were calibrated for temperature using indium. Sample tests of DSC experiments were carried out in the conventional mode at a heating rate of 5-10° C. $min^{-1}$ with the temperature ranging from 25 to 200° C.

Thermogravimetric (TG) curves, were obtained by using Perkin-Elmer Thermal TGA7, with $N_2$ as a purge gas at a flow rate of 50 mL $min^{-1}$, the heating rate is 10° C./min.

Example 1 Preparation of Form I of the Compound of Formula A 95 mg of the compound of Formula A was dissolved in 36 mL of acetone under heating and stirring, filtered while hot, cooled the filtrate naturally to room temperature, filtered out the precipitates, dried at 60° C. under vacuum, got the white powder 64 mg, yield 67.4%, m.p. (DSC): 247.31-248.33° C.

The obtained powder sample is Form I of the compound of Formula A, the powder X-ray diffractogram of which is shown in FIG. 1, and the main data are shown in Table 1. Peaks (2θ) chosen from the figure has the following values: 5.302, 7.313, 10.684, 13.862, 14.590, 15.194, 16.304, 17.528, 19.165, 19.876, 21.137, 21.394, 23.145, 25.809, 26.458, each of the diffraction angles having an error of about ±0.2 degrees (2θ), wherein characteristic peaks (2θ) are identified as 5.302, 10.684, 13.862, and 14.590.

DSC testing shows that the melting point range of the Form I obtained is 247.31-248.33° C.

TABLE 1

| # | 2θ | Height | I % | Area | I % |
|---|---|---|---|---|---|
| 1 | 5.302 | 4006 | 86.7 | 33918 | 88.4 |
| 2 | 7.313 | 1399 | 30.3 | 11679 | 30.5 |
| 3 | 10.684 | 3495 | 75.6 | 29404 | 76.7 |
| 4 | 13.862 | 4620 | 100.0 | 38350 | 100.0 |
| 5 | 14.590 | 1856 | 40.2 | 15491 | 40.4 |
| 6 | 15.194 | 306 | 6.6 | 1096 | 2.9 |
| 7 | 16.304 | 663 | 14.4 | 4800 | 12.5 |
| 8 | 19.876 | 1540 | 33.3 | 12970 | 33.8 |
| 9 | 21.137 | 499 | 10.8 | 3651 | 9.5 |
| 10 | 21.394 | 622 | 13.5 | 5417 | 14.1 |
| 11 | 23.145 | 697 | 15.1 | 16722 | 43.6 |
| 12 | 23.345 | 612 | 13.2 | 20885 | 54.5 |
| 13 | 25.809 | 1474 | 31.9 | 26498 | 69.1 |

Example 2 Preparation of Form I of the Compound of Formula A 100 mg of the compound of Formula A was dissolved in 25 mL of methyl ethyl ketone under heating and stirring, then stopped heating, the solution was cooled naturally to room temperature, the solid was collected by filtration to obtain the Form I of the compound of Formula A. The powder X-ray diffractogram of the sample obtained by this method is the same as that of the Form I of the compound of Formula A obtained in Example 1.

Example 3 Preparation of Form I of the Compound of Formula A 100 mg of the compound of Formula A was dissolved in 20 mL of n-propanol under heating and stirring, then stopped heating, the solution was cooled naturally to room temperature, the solid was collected by filtration to obtain the Form I of the compound of Formula A.

The powder X-ray diffractogram of the sample obtained by this method is the same as that of the Form I of the compound of Formula A obtained in Example 1.

Example 4 Preparation of Form I of the Compound of Formula A 96.5 mg of the compound of Formula A was dissolved in 25 mL of toluene under heating and stirring, then cooled the solution naturally to room temperature, filtered out the precipitates, dried at 60° C. under vacuum, got the white powder 75.8 mg, yield 78.5%.

The powder X-ray diffractogram of the sample obtained by this method is the same as that of the Form I of the compound of Formula A obtained in Example 1.

Example 5 Preparation of Form I of the Compound of Formula A 524.5 mg of the compound of Formula A was dissolved in 18 mL of N,N-dimethylformamide under heating and stirring, then cooled the solution naturally to room temperature, crystals appeared at about 60° C., then stirred overnight, filtered out the precipitates, got the white powder 449.2 mg, yield 85.6%.

The powder X-ray diffractogram of the sample obtained by this method is the same as that of the Form I of the compound of Formula A obtained in Example 1.

Example 6 Preparation of Form I of the Compound of Formula A 0.5 g of the compound of Formula A was dissolved in mixture solvents of 250 mL of methanol and 500 mL of water under heating and stirring, then cooled the solution naturally to room temperature, filtered out the precipitates, got the white powder 0.42 g, yield 84%.

The powder X-ray diffractogram of the sample obtained by this method is the same as that of the Form I of the compound of Formula A obtained in Example 1.

Example 7 Preparation of Form I of the Compound of Formula A 100 mg of the compound of Formula A was dissolved in mixture solvents of 22 mL of ethanol and 44 mL of water under heating and stirring, and then cooled the solution naturally to room temperature, and the solid was collected by filtration.

The powder X-ray diffractogram of the sample obtained by this method is the same as that of the Form I of the compound of Formula A obtained in Example 1.

Example 8 Preparation of Form I of the Compound of Formula A 0.51 g of the compound of Formula A was dissolved in mixture solvents of 200 mL of acetonitrile and 400 mL of water under heating and stirring, then cooled the solution naturally to room temperature, filtered out the precipitates, got the white powder 0.36 g, yield 70%.

The powder X-ray diffractogram of the sample obtained by this method is the same as that of the Form I of the compound of Formula A obtained in Example 1.

Example 9 Preparation of Form I of the Compound of Formula A

The pre-mixed solvents of acetone and tetrahydrofuran in a volume ratio of 5:1 was added gradually to a flask containing the compound of Formula A, heated it to mild reflux, stirred it, and added above mixed solvents constantly till the compound of Formula A was totally dissolved finally, then cooled the solution naturally to room temperature; the precipitated solid was collected by filtration, got the white powder. The powder X-ray diffractogram of the sample obtained by this method is the same as that of the Form I of the compound of Formula A obtained in Example 1.

Example 10 Preparation of Form I of the Compound of Formula A

The pre-mixed solvents of acetone and tetrahydrofuran in a volume ratio of 1:7 was added gradually to a flask containing the compound of Formula A, heated it to mild reflux, stirred it, and added above mixed solvents constantly till the compound of Formula A was totally dissolved finally, then cooled the solution naturally to room temperature; the precipitated solid was collected by filtration, got the white powder. The powder X-ray diffractogram of the sample obtained by this method is the same as that of the Form I of the compound of Formula A obtained in Example 1.

Example 11 Preparation of Form I of the Compound of Formula A 50 mg of the compound of Formula A was dissolved in 6 mL of mixture solvents of tetrahydrofuran and acetonitrile in a volume ratio of 1:3 under heating and stirring, then stopped heating and cooled the solution naturally to room temperature, standed for crystallization; and the precipitates were collected by filtration to obtain the Form I of the compound of Formula A.

The powder X-ray diffractogram of the sample obtained by this method is the same as that of the Form I of the compound of Formula A obtained in Example 1.

Example 12 Preparation of Form I of the Compound of Formula A 200 mg of the compound of Formula A was dissolved in 26 mL mixture solvents of tetrahydrofuran and acetonitrile in a volume ratio of 1:7 under heating and stirring, then stopped heating and cooled the solution naturally to 25° C.; then put the mixture to ultrasonic for 15 minutes; after that the mixture was reheated to 60-65° C. to dissolve most of the precipitates, then cooled the solution to room temperature, again reheated to 60-65° C. to dissolve most of the precipitates, and then cooled the mixture to room temperature for precipitating completely; the precipitates were collected by filtration.

The powder X-ray diffractogram of the sample obtained by this method is the same as that of the Form I of the compound of Formula A obtained in Example 1.

Example 13 Preparation of Form I of the Compound of Formula A 0.5 g of the compound of Formula A was dissolved in solvent mixture of 20 mL dichloromethane, 5 mL acetic acid and 25 mL n-heptane by stirring at room temperature, continued stirring for about another 5-6 hrs, the solid precipitated, and then continued stirring at 25-30° C. for another 48 hrs. The solid was collected by filtration, and then dried.

The powder X-ray diffractogram of the sample obtained by this method is the same as that of the Form I of the compound of Formula A obtained in Example 1.

Example 14 Preparation of Form I of the Compound of Formula A 79 mg of the compound of Formula A was dissolved in 16 mL of isopropanol under heating and stirring, then to the solution 20 mL of water was added slowly, then cooled the solution naturally to room temperature; the precipitate was collected by filtration, and dried at 60° C. under vacuum, got white powder 77.5 mg, yield 98.1%. The powder X-ray diffractogram of the sample obtained by this method is the same as that of the Form I of the compound of Formula A obtained in Example 1.

Example 15 Preparation of Form I of the Compound of Formula A 100 mg of the compound of Formula A was dissolved in 10 mL of dichloromethane under heating and stirring, to the solution 20 mL of ethyl acetate was added slowly; the product was precipitated out by cooling the solution naturally to 40° C., then the solid was collected by filtration.

The powder X-ray diffractogram of the sample obtained by this method is the same as that of the Form I of the compound of Formula A obtained in Example 1.

Example 16 Preparation of Form I of the Compound of Formula A

Dissolved 2 g of the compound of Formula A in 688 mL acetone under heating and stirring, filtrated the hot solution, then to the solution 752 mL of n-heptane was added slowly under refluxing and stirring, stopped heating, the solution was cooled naturally under stirring for 3-4 hrs, filtered the precipitates, dried at 60° C. under vacuum for 2 hrs, got crystalline white solid.

The powder X-ray diffractogram of the sample obtained by this method is the same as that of the Form I of the compound of Formula A obtained in Example 1.

Example 17 Preparation of Form I of the Compound of Formula A 100 mg of the compound of Formula A was dissolved in 10 mL of dichloromethane under heating and stirring, to the solution was added 10 mL of n-heptane slowly, the product precipitated, and was collected by filtration.

The powder X-ray diffractogram of the sample obtained by this method is the same as that of the Form I of the compound of Formula A obtained in Example 1.

Example 18 Preparation of Form I of the Compound of Formula A 0.2 g of the compound of Formula A was dissolved in 20 mL of DMSO under heating and stirring, then 9 mL of water was added in dropwise, cooled to room temperature, and the product precipitated, and was collected by filtration.

The powder X-ray diffractogram of the sample obtained by this method is the same as that of the Form I of the compound of Formula A obtained in Example 1.

Example 19 Preparation of Form I of the Compound of Formula A 88 mg of the compound of Formula A was dissolved in 2.0 mL of DMF under heating and stirring, and 1.5 mL of water was added to the solution slowly; then heated to get a clear solution, then cooled to room temperature for precipitation, filtered out the precipitates, dried at 60° C. under vacuum, got the solid sample.

The powder X-ray diffractogram of the sample obtained by this method is the same as that of the Form I of the compound of Formula A obtained in Example 1.

Example 20 Preparation of Form I of the Compound of Formula A 94 mg of the compound of Formula A was dissolved in 35 mL of acetone under heating and stirring, then to the solution was added 40 mL of water slowly, then cooled the solution to room temperature for precipitation, filtered out the precipitates, dried at 60° C. under vacuum overnight, got the solid sample.

The powder X-ray diffractogram of the sample obtained by this method is the same as that of the Form I of the compound of Formula A obtained in Example 1.

Example 21 Preparation of Form I of the Compound of Formula A 2.8 g of the compound of Formula A was dissolved in 600 mL of ethanol under heating and stirring, to the solution 1200 mL of water was added slowly, maintained the solution temperature not lower than 60° C. and filtered through filter paper, the filtrate was stirred at room temperature overnight for precipitation. The solid was collected by filtration, dried at 60° C. under vacuum overnight, got the solid sample.

The powder X-ray diffractogram of the sample obtained by this method is the same as that of the Form I of the compound of Formula A obtained in Example 1.

Example 22 Preparation of Form I of the Compound of Formula A 111.54 mg of the compound of Formula A was suspended in 22 mL of mixture solvents of acetone/water (1/1, V/V), and stirred at 60° C. for 20 hrs. Then stopped heating, and the solid was collected by filtration.

The powder X-ray diffractogram of the sample obtained by this method is the same as that of the Form I of the compound of Formula A obtained in Example 1.

Example 23 Preparation of Form I of the Compound of Formula A 50 mg of Form I of the compound of Formula A and 2.5 mg of Form II of the compound of Formula A were suspended in 5 mL of mixture solvents of ethanol/water (1/3, V/V) and stirred at 60° C. for 20 hrs, then stopped heating, and the solid was collected by filtration.

The powder X-ray diffractogram of the sample obtained by this method is the same as that of the Form I of the compound of Formula A obtained in Example 1.

Example 24 Preparation of Form I of the Compound of Formula A 91.6 mg of Form I of the compound of Formula A and 92.0 mg of Form III of the compound of Formula A were suspended in 8 mL of mixture solvents of ethanol/water (1/9, V/V) and stirred at 40° C. overnight, then stopped heating, and the solid was collected by filtration.

The powder X-ray diffractogram of the sample obtained by this method is the same as that of the Form I of the compound of Formula A obtained in Example 1.

Example 25 Preparation of Form I of the Compound of Formula A 3.1 g of mix crystalline forms of the compound of Formula A consisting of Form I and Form III was suspended in 77.5 mL of acetone, heated to reflux under stirring for 16 hrs; then stopped heating, and the solid was collected by filtration.

The powder X-ray diffractogram of the sample obtained by this method is the same as that of the Form I of the compound of Formula A obtained in Example 1.

Example 26 Preparation of Form II of Hemiethanol Solvate of the Compound of Formula A 1.0 g of the compound of Formula A was dissolved in 600 mL of ethanol by heating to reflux under stirring, and then cooled the solution to room temperature; and the solid was collected by filtration, dried at 55° C. under vacuum for 6 hours, Form II of hemiethanol solvate of the compound of Formula A was got, m.p. (DSC): 245.7-247.0° C.

The obtained powder sample is Form II of hemiethanol solvate of the compound of Formula A, the powder X-ray diffractogram of which is shown in FIG. 4, and the main data are shown in Table 2. Peaks (2θ) chosen from the figure has the following values: 4.243, 4.600, 5.172, 7.243, 8.231, 8.862, 9.259, 10.343, 11.430, 12.080, 13.165, 13.995, 14.586, 16.148, 17.113, 18.239, 18.911, 20.372, 22.087, 23.488, 24.772, and 26.176, each of the diffraction angles having an error of about ±0.2 degrees (2θ), wherein characteristic peaks (2θ) are identified as 8.231, 10.343, 12.080, and 13.165.

DSC curve shows that the melting point range of the Form II obtained is 245.7-247.0° C. as shown in FIG. 5.

TGA curve shows that the Form II obtained is hemiethanol solvate as shown in FIG. 6.

$^1$H NMR (400 MHz, $CDCl_3$) δ 8.59 (s, 1H), 7.69 (d, J=8.5 Hz, 1H), 7.56 (s, 1H), 7.38 (d, J=2.1 Hz, 1H), 7.32 (s, 1H), 7.19 (dd, J=8.5, 2.1 Hz, 1H), 4.06 (d, J=3.3 Hz, 7H), 3.70 (d, J=7.9 Hz, 1H), 3.05 (d, J=4.9 Hz, 3H), 2.72 (s, 3H), 1.27 (s, 1H), 1.22 (t, J=7.0 Hz, 1H).

TABLE 2

| # | 2θ | Height | I % | Area | I % |
|---|---|---|---|---|---|
| 1 | 4.243 | 4433 | 29.3 | 56888 | 25.6 |
| 2 | 4.600 | 1942 | 12.8 | 18713 | 8.4 |
| 3 | 5.172 | 1232 | 8.1 | 2410 | 1.1 |
| 4 | 7.243 | 1344 | 8.9 | 7622 | 3.4 |
| 5 | 8.231 | 11989 | 79.3 | 192553 | 86.6 |
| 6 | 8.862 | 2058 | 13.6 | 21656 | 9.7 |
| 7 | 9.259 | 3245 | 21.5 | 35380 | 15.9 |
| 8 | 10.343 | 7843 | 51.8 | 98631 | 44.3 |
| 9 | 11.430 | 2043 | 13.5 | 13764 | 6.2 |
| 10 | 12.080 | 13569 | 89.7 | 169759 | 76.3 |
| 11 | 13.165 | 15128 | 100.0 | 222476 | 100.0 |
| 12 | 14.586 | 7078 | 46.8 | 87027 | 39.1 |
| 13 | 18.239 | 5229 | 34.6 | 65146 | 29.3 |
| 14 | 18.911 | 2288 | 15.1 | 21311 | 9.6 |
| 15 | 20.372 | 2524 | 16.7 | 21225 | 9.5 |
| 16 | 22.087 | 2052 | 13.6 | 20523 | 9.2 |
| 17 | 23.488 | 2990 | 19.8 | 23463 | 10.5 |
| 18 | 26.176 | 2719 | 18.0 | 35243 | 15.8 |

Example 27 Preparation of Form II of Hemiethanol Solvate of the Compound of Formula A 112.7 mg of the compound of Formula A was dissolved in 35 mL of ethanol under heating and stirring, then to the solution was added 70 mL of n-heptane slowly; then cooled the solution to room temperature and stirred overnight; the solid was collected by filtration, Form II of hemiethanol solvate of the compound of Formula A was got.

The powder X-ray diffractogram of the sample obtained by this method is the same as that of the Form II of hemiethanol solvate of the compound of Formula A obtained in Example 26.

Example 28 Preparation of Form II of Hemiethanol Solvate of the Compound of Formula A 0.6 g of the compound of Formula A was dissolved in mixture solvents of 36 mL of ethanol and 12 mL of acetic acid under heating and stirring, then to the solution was added 48 mL of n-heptane in dropwise, cooled to room temperature and stirred for 3 hrs. The solid was collected by filtration, and dried under ambient temperature. The powder X-ray diffractogram of the sample obtained by this method is the same as that of the Form II of hemiethanol solvate of the compound of Formula A obtained in Example 26.

Example 29 Preparation of Form II of Hemiethanol Solvate of the Compound of Formula A 1.3 g of the compound of Formula A was suspended in 450 mL of mixture solvents of ethanol/tetrahydrofuran (2/1 in V/V), heated by heating to reflux to dissolve it, then cooled to 20-30° C. slowly, then stirred at 20-30° C. for 16 hrs. The solid was collected by filtration, and dried under ambient temperature for 24 hrs, then dried under vacuum at 55° C. for 5 hrs.

The powder X-ray diffractogram of the sample obtained by this method is the same as that of the Form II of hemiethanol solvate of the compound of Formula A obtained in Example 26.

Example 30 Preparation of Form II of Hemiethanol Solvate of the Compound of Formula A 1.0 g of the compound of Formula A was suspended in 306 mL of mixture solvents of ethanol/tetrahydrofuran (5/1 in V/V), heated by heating to reflux to dissolve it, then cooled to 20-30° C. slowly, then stirred at 20-30° C. for 16 hrs. The solid was collected by filtration.

The powder X-ray diffractogram of the sample obtained by this method is the same as that of the Form II of hemiethanol solvate of the compound of Formula A obtained in Example 26.

Example 31 Preparation of Form II of Hemiethanol Solvate of the Compound of Formula A 86 mg of Form IV of the compound of Formula A was suspended in 2 mL of ethanol and stirred at 40° C. for 3 days, the solid was collected by filtration.

The powder X-ray diffractogram of the sample obtained by this method is the same as that of the Form II of hemiethanol solvate of the compound of Formula A obtained in Example 26.

Example 32 Preparation of Form II of Hemiethanol Solvate of the Compound of Formula A A mixture of 25 mg of Form I and 25 mg of Form II of the compound of Formula A was suspended in solvent mixture of 2 mL n-heptane and 0.5 mL ethanol, the suspension was stirred at room temperature for 3 days, the solid was collected by filtration.

The powder X-ray diffractogram of the sample obtained by this method is the same as that of the Form II of hemiethanol solvate of the compound of Formula A obtained in Example 26.

Example 33 Preparation of Form II of Hemiethanol Solvate of the Compound of Formula A A mixture of 50 mg of Form I, 50 mg of Form II and 50 mg of Form III of the compound of Formula A was suspended in solvent mixture of 2 mL ethanol and 0.5 mL water, then heated to 60° C. and stirred at 60° C. for 24 hrs, the solid was collected by filtration.

The powder X-ray diffractogram of the sample obtained by this method is the same as that of the Form II of hemiethanol solvate of the compound of Formula A obtained in Example 26.

Example 34 Preparation of Form III of the Compound of Formula A 1.2 g of the compound of Formula A was suspended in proper amount of mixture solvents of tetrahydrofuran and water (1/1, V/V), heated to reflux under stirring to dissolve the compound of Formula A, and then the solution was cooled to room temperature and stirred for 20 hrs. The solid was collected by filtration, and Form III of the compound of Formula A was got, m.p. (DSC): 248.04-249.00° C.

The obtained powder sample is Form III of the compound of Formula A, the powder X-ray diffractogram of which is shown in FIG. 7, and the main data are shown in Table 3. Peaks (2θ) chosen from the figure has the following values: 4.872, 7.199, 8.619, 9.756, 10.586, 12.028, 14.415, 15.163, 16.189, 20.426, 22.357, 24.253, 24.882, 25.411, and 26.082, each of the diffraction angles having an error of about ±0.2 degrees (2θ), wherein characteristic peaks (2θ) are identified as 7.199, 8.619, 14.415, and 15.163.

DSC curve shows that the melting point range of the Form III of the compound of Formula A is 248.04-249.00° C. as shown in FIG. 8.

TABLE 3

| # | 2θ | Height | I % | Area | I % |
|---|---|---|---|---|---|
| 1 | 4.872 | 1489 | 9.4 | 17428 | 8.4 |
| 2 | 7.199 | 6222 | 39.1 | 81265 | 39.3 |
| 3 | 8.619 | 12272 | 77.2 | 173969 | 84.2 |
| 4 | 12.028 | 3635 | 22.9 | 44392 | 21.5 |
| 5 | 14.415 | 7237 | 45.5 | 104182 | 50.4 |
| 6 | 15.163 | 15894 | 100.0 | 206710 | 100.0 |
| 7 | 16.189 | 2087 | 13.1 | 23216 | 11.2 |
| 8 | 17.293 | 724 | 4.6 | 3832 | 1.9 |
| 9 | 19.895 | 1152 | 7.2 | 15781 | 7.6 |
| 10 | 20.426 | 2989 | 18.8 | 39459 | 19.1 |
| 11 | 22.357 | 3084 | 19.4 | 51058 | 24.7 |
| 12 | 23.993 | 1951 | 12.3 | 22113 | 10.7 |
| 13 | 24.253 | 1802 | 11.3 | 39616 | 19.2 |
| 14 | 24.882 | 1598 | 10.1 | 6668 | 3.2 |
| 15 | 25.411 | 2941 | 18.5 | 20619 | 10.0 |
| 16 | 26.082 | 4601 | 28.9 | 56578 | 27.4 |
| 17 | 29.101 | 2397 | 15.1 | 31862 | 15.4 |
| 18 | 32.688 | 1107 | 7.0 | 11840 | 5.7 |

Example 35 Preparation of Form III of the Compound of Formula A 1.7 g of the compound of Formula A was suspended in 70 mL of mixture solvents of tetrahydrofuran and water (3/1, V/V), heated to reflux under stirring to dissolve the compound of Formula A, then cooled the solution to room temperature slowly, the solid was collected by filtration.

The powder X-ray diffractogram of the sample obtained by this method is the same as that of the Form III of the compound of Formula A obtained in Example 34.

Example 36 Preparation of Form III of the Compound of Formula A 1.25 g of the compound of Formula A was suspended in 500 mL of mixture solvents of tetrahydrofuran and water (1/2.57, V/V), heated to reflux under stirring to dissolve the compound of Formula A, then cooled the solution to room temperature slowly, stirred at 20-30° C. for 16 hrs, the solid was collected by filtration.

The powder X-ray diffractogram of the sample obtained by this method is the same as that of the Form III of the compound of Formula A obtained in Example 34.

Example 37 Preparation of Form III of the Compound of Formula A 40 mg of the compound of Formula A was suspended in 13 mL of mixed solvents of acetonitrile and water (1/1, V/V), heated to 72° C. under stirring to dissolve the compound of Formula A; then the solution was cooled to room temperature slowly, and the solid was collected by filtration.

The powder X-ray diffractogram of the sample obtained by this method is the same as that of the Form III of the compound of Formula A obtained in Example 34.

Example 38 Preparation of Form III of the Compound of Formula A 53 mg of the compound of Formula A was suspended in 5.2 mL of mixed solvent of acetonitrile and water (7/1, V/V), heated to 72° C. under stirring to dissolve the compound of Formula A; then the solution was cooled to room temperature slowly, and the solid was collected by filtration.

The powder X-ray diffractogram of the sample obtained by this method is the same as that of the Form III of the compound of Formula A obtained in Example 34.

Example 39 Preparation of Form IV of Monoacetic Acid Solvate of the Compound of Formula A 3.0 g of the compound of Formula A was suspended in 60 mL of dichloromethane and heated to reflux under stirring, then to the suspension 12 mL of acetic acid was added, the suspended solid dissolved to obtain clarified solution; then 120 mL of n-heptane was added by dropwise at refluxing temperature, after the addition completed, the obtained mixture was stirred under reflux for 1 hr, then cooled to 20-30° C. slowly; after stirred at 20-30° C. for 16 hrs, the solid was collected by filtration, then dried for 1 day under ambient condition, and Form IV of monoacetic acid solvate of the compound of Formula A was got, m.p. (DSC): 245.1-247.4° C.

The obtained powder sample is Form IV of monoacetic acid solvate of the compound of Formula A, the powder X-ray diffractogram of which is shown in FIG. 10, and the main data are shown in Table 4. Peaks (2θ) chosen from the figure has the following values: 5.724, 7.601, 10.071, 10.501, 11.488, 13.322, 15.358, 16.305, 17.331, 18.098, 20.152, 21.202, 22.720, 26.373, and 26.865, each of the diffraction angles having an error of about ±0.2 degrees (2θ), wherein characteristic peaks (2θ) are identified as 5.724, 7.601, 10.501, and 11.488.

DSC curve shows that the melting point range of the Form IV of monoacetic acid solvate of the compound of Formula A is 245.1-247.4° C. as shown in FIG. 11. TGA curve shows that the Form IV obtained is monoacetic acid solvate as shown in FIG. 12.

$^1$H NMR (400 MHz, $CDCl_3$) δ 8.60 (s, 1H), 7.70 (d, J=8.5 Hz, 1H), 7.57 (s, 1H), 7.39 (d, J=2.0 Hz, 1H), 7.37 (s, 1H), 7.20 (dd, J=8.5, 2.1 Hz, 1H), 4.07 (d, J=2.1 Hz, 7H), 3.06 (d, J=4.9 Hz, 3H), 2.73 (s, 3H), 2.08 (s, 3H).

TABLE 4

| # | 2θ | Height | I % | Area | I % |
|---|---|---|---|---|---|
| 1 | 5.724 | 12068 | 62.6 | 176947 | 75.7 |
| 2 | 7.601 | 8273 | 42.9 | 109210 | 46.7 |
| 3 | 10.071 | 7520 | 39.0 | 106430 | 45.5 |
| 4 | 10.501 | 15789 | 81.8 | 189592 | 81.1 |
| 5 | 11.488 | 19293 | 100.0 | 233846 | 100.0 |
| 6 | 13.322 | 2388 | 12.4 | 23998 | 10.3 |
| 7 | 15.358 | 6048 | 31.3 | 69472 | 29.7 |
| 8 | 16.305 | 844 | 4.4 | 2365 | 1.0 |
| 9 | 17.331 | 4993 | 25.9 | 52614 | 22.5 |
| 10 | 18.098 | 1214 | 6.3 | 4800 | 2.1 |
| 11 | 20.152 | 4433 | 23.0 | 42594 | 18.2 |

TABLE 4-continued

| # | 2θ | Height | I % | Area | I % |
|---|---|---|---|---|---|
| 12 | 21.202 | 2314 | 12.0 | 17590 | 7.5 |
| 13 | 22.088 | 1310 | 6.8 | 5597 | 2.4 |
| 14 | 22.720 | 2829 | 14.7 | 26114 | 11.2 |
| 15 | 26.373 | 1600 | 8.3 | 8644 | 3.7 |
| 16 | 26.865 | 1668 | 8.6 | 11143 | 4.8 |
| 17 | 29.685 | 1231 | 6.4 | 6018 | 2.6 |
| 18 | 31.029 | 1092 | 5.7 | 4810 | 2.1 |
| 19 | 31.974 | 963 | 5.0 | 3321 | 1.4 |
| 20 | 32.944 | 1196 | 6.2 | 10222 | 4.4 |

Example 40 Preparation of Form IV of Monoacetic Acid Solvate of the Compound of Formula A 0.5 g of the compound of Formula A was suspended in mixture solvents of 10 mL of dichloromethane and 2 mL of acetic acid, heated to reflux under stirring to dissolve it, then 20 mL of n-heptane was added to the refluxing solution, the solution was continue to reflux for 5 hrs; huge amount of solid was precipitated, the suspension was cooled to 20-30° C. slowly and continued stirring for another 18 hrs, and the solid was collected by filtration.

The powder X-ray diffractogram of the sample obtained by this method is the same as that of the Form IV of monoacetic acid solvate of the compound of Formula A obtained in Example 39.

Example 41 Preparation of Form IV of Monoacetic Acid Solvate of the Compound of Formula A 0.5 g of the compound of Formula A was suspended in 10 mL of acetic acid, heated to 90° C. under stirring to dissolve it, then 20 mL of n-heptane was added to the solution; the solution was continue stirring at 90° C. for another 1 hr, then cooled to 20-30° C. slowly, huge amount of solid was precipitated, after that heated to 90° C. and stirred for 2 hrs, then cooled to 20-30° C. and stirred at that temperature for 18 hrs, the solid was collected by filtration.

The powder X-ray diffractogram of the sample obtained by this method is the same as that of the Form IV of monoacetic acid solvate of the compound of Formula A obtained in Example 39.

Example 42 Preparation of Form VII of the Compound of Formula A 2.0 g of the compound of Formula A was suspended in 180 mL of mixture solvents of THF/H2O (1/1, V/V), heated under stirring to dissolve it; then the solution was cooled to ambient temperature slowly, and the solid was collected by filtration, dried at ambient temperature for 3 days, then under vacuum at 55° C. for 16 hrs, and Form VII of the compound of Formula A was got, m.p. (DSC): 245.4-247.8° C.

The obtained powder sample is Form VII of the compound of Formula A, the powder X-ray diffractogram of which is shown in FIG. 13, and the main data are shown in Table 5. Peaks (2θ) chosen from the figure has the following values: 5.883, 6.751, 7.145, 8.981, 11.784, 13.620, 14.942, 18.160, 21.356, 23.687, 27.476, 28.129, and 29.077, each of the diffraction angles having an error of about ±0.2 degrees (2θ), wherein characteristic peaks (2θ) are identified as 8.981, 11.784, and 13.620. DSC curve shows that the melting point range of the Form VII of the compound of Formula A is 245.4-247.8° C. as shown in FIG. 14.

TABLE 5

| # | 2θ | Height | I % | Area | I % |
|---|---|---|---|---|---|
| 1 | 5.883 | 1668 | 2.5 | 3924 | 0.3 |
| 2 | 6.751 | 2855 | 4.2 | 46239 | 3.9 |
| 3 | 7.145 | 1776 | 2.6 | 15044 | 1.3 |
| 4 | 8.981 | 17600 | 25.9 | 339184 | 28.8 |
| 5 | 11.784 | 9042 | 13.3 | 124406 | 10.6 |
| 6 | 13.620 | 68003 | 100.0 | 1178676 | 100.0 |
| 7 | 14.942 | 6867 | 10.1 | 132891 | 11.3 |
| 9 | 18.160 | 5657 | 8.3 | 89446 | 7.6 |
| 10 | 19.087 | 1581 | 2.3 | 10973 | 0.9 |
| 11 | 19.719 | 1088 | 1.6 | 1398 | 0.1 |
| 12 | 21.356 | 3021 | 4.4 | 28801 | 2.4 |
| 14 | 23.687 | 4944 | 7.3 | 110027 | 9.3 |
| 15 | 26.037 | 2416 | 3.6 | 24436 | 2.1 |
| 16 | 27.476 | 2684 | 3.9 | 47713 | 4.0 |
| 17 | 28.129 | 2525 | 3.7 | 17520 | 1.5 |
| 18 | 29.077 | 1528 | 2.2 | 8260 | 0.7 |
| 19 | 29.962 | 1516 | 2.2 | 9989 | 0.8 |

Example 43 Preparation of Form VIII of Monodioxane Solvate of the Compound of Formula A 1.2 g of the compound of Formula A was suspended in 100 mL of dioxane, heated under stirring to dissolve it, then the solution was cooled to room temperature slowly, and the solid was collected by filtration, dried at room temperature for 2 days, and Form VIII of monodioxane solvate of the compound of Formula A was got, m.p. (DSC): 245.6-248.3° C.

The obtained powder sample is Form VIII of monodioxane solvate of the compound of Formula A, the powder X-ray diffractogram of which is shown in FIG. 16, and the main data are shown in Table 6. Peaks (2θ) chosen from the figure has the following values: 5.723, 8.151, 9.040, 14.507, 16.304, 16.797, 17.923, 21.894, 22.859, 23.744, 24.535, 25.897, 29.154, and 29.846, each of the diffraction angles having an error of about ±0.2 degrees (2θ), wherein characteristic peaks (2θ) are identified as 9.040, 14.507, 16.304, and 16.797.

DSC curve shows that the melting point range of the Form VIII of monodioxane solvate of the compound of Formula A is 245.6-248.3° C. as shown in FIG. 17. TGA curve shows that the Form VIII obtained is monodioxane solvate as shown in FIG. 18.

$^1$H NMR (400 MHz, $CDCl_3$) δ 8.60 (s, 1H), 7.70 (d, J=8.5 Hz, 1H), 7.57 (s, 1H), 7.39 (s, 1H), 7.32 (s, 1H), 7.20 (d, J=8.5 Hz, 1H), 4.06 (s, 7H), 3.69 (s, 6H), 3.06 (d, J=4.9 Hz, 3H), 2.73 (s, 3H).

TABLE 6

| # | 2θ | Height | I % | Area | I % |
|---|---|---|---|---|---|
| 1 | 5.723 | 3053 | 7.6 | 38921 | 6.1 |
| 2 | 8.151 | 10273 | 25.5 | 140952 | 22.2 |
| 3 | 9.040 | 40245 | 100.0 | 635118 | 100.0 |
| 4 | 11.408 | 1733 | 4.3 | 14192 | 2.2 |
| 5 | 12.671 | 1566 | 3.9 | 18587 | 2.9 |
| 6 | 14.507 | 18594 | 46.2 | 302955 | 47.7 |
| 7 | 16.304 | 28034 | 69.7 | 463416 | 73.0 |
| 8 | 16.797 | 22288 | 55.4 | 404179 | 63.6 |
| 9 | 17.923 | 2176 | 5.4 | 16686 | 2.6 |
| 10 | 20.330 | 1949 | 4.8 | 24582 | 3.9 |
| 11 | 21.576 | 1913 | 4.8 | 3676 | 0.6 |
| 12 | 21.894 | 2654 | 6.6 | 18101 | 2.9 |
| 13 | 22.859 | 5853 | 14.5 | 67737 | 10.7 |
| 14 | 23.744 | 2354 | 5.8 | 18622 | 2.9 |
| 15 | 24.535 | 2654 | 6.6 | 27094 | 4.3 |

TABLE 6-continued

| # | 2θ | Height | I % | Area | I % |
|---|---|---|---|---|---|
| 16 | 25.897 | 5589 | 13.9 | 96150 | 15.1 |
| 17 | 29.154 | 3060 | 7.6 | 38451 | 6.1 |
| 18 | 29.846 | 2765 | 6.9 | 26744 | 4.2 |
| 19 | 33.913 | 1172 | 2.9 | 7284 | 1.1 |
| 20 | 37.442 | 1026 | 2.5 | 7913 | 1.2 |

Example 44 Stability of Form I Under High Temperature, High Humidity and Illumination Conditions Determination method: the test sample of Form I prepared in Example 1 was added to a culture dish, which was uncovered and put in a sealed clean container; then the container was placed under the conditions of the temperature of 60° C., the temperature of 25° C. and the relative humidity of 92.5%±5%, and the illumination of 4500 lx±500 lx respectively for 10 days; then sampled, investigated the purity and crystalline form of the sample, and compared the results of the investigation, which were shown in the following table.

Results of Influence factor experiment of Form 1 (10 days)

| | 0 day | | 60° C. | | 92.5 ± 5% RH | | 4500 lx ± 500 lx | |
|---|---|---|---|---|---|---|---|---|
| Form | Purity A% | Form | Purity A% | Form | Purity A% | Form | Purity A% | Form |
| I | 98.94 | I | 98.94 | I | 98.94 | I | 98.94 | I |

Conclusion: the data in the table illustrate that, the chemical purity and crystalline form of the Form I are not changed after placed under high temperature, high humidity and illumination conditions for 10 days, the Form I is stable.

To be understood, the examples and embodiments described herein are only for interpretation purposes, and various improvements or changes in view of these will be suggested to those skilled in the art and are within the subject and scope of present application and the scope of the claims. All publications, patents and patent applications cited herein by the way of reference are incorporated into this article and for all purposes.

What is claimed is:

1. A solvate of 6-((6, 7-dimethoxyquinazolin-4-yl)oxy)-N, 2-dimethylbenzofuran-3-carboxamide, wherein said solvate is ethanol solvate.

2. The solvate of claim 1, wherein the ethanol solvate is hemiethanol solvate.

3. The solvate of claim 2, wherein the ethanol solvate is in a substantially crystalline form.

4. The solvate of claim 3, wherein the crystalline form is polymorphic Form II.

5. The solvate of claim 4 wherein Form II comprises X-ray powder diffraction pattern having characteristic peaks expressed in degrees 2-theta at 8.2, 10.3, 12.1, and 13.2, each of the diffraction angles having an error of about ±0.2 degrees (2θ).

6. The solvate of claim 4 wherein Form II comprises X-ray powder diffraction pattern having characteristic peaks expressed in degrees 2-theta at 4.2 degrees, 4.6 degrees, 7.2 degrees, 8.2 degrees, 9.3 degrees, 10.3 degrees, 12.1 degrees, 13.2 degrees, 14.6 degrees, and 18.2 degrees, each of the diffraction angles having an error of about ±0.2 degrees (2θ).

7. The solvate of claim 4 wherein Form II comprises X-ray powder diffraction pattern having characteristic peaks expressed in degrees 2-theta at 4.2 degrees, 4.6 degrees, 5.2 degrees, 7.2 degrees, 8.2 degrees, 9.3 degrees, 10.3 degrees, 12.1 degrees, 13.2 degrees, 14.6 degrees, 18.2 degrees, and 23.5 degrees, each of the diffraction angles having an error of about ±0.2 degrees (2θ).

8. The solvate of claim 4 wherein Form II comprises X-ray powder diffraction pattern having characteristic peaks expressed in degrees 2-theta at 4.2 degrees, 4.6 degrees, 5.2 degrees, 7.2 degrees, 8.2 degrees, 8.9 degrees, 9.3 degrees, 10.3 degrees, 11.4 degrees, 12.1 degrees, 13.2 degrees, 14.6 degrees, 18.2 degrees, 18.9 degrees, 20.4 degrees, 22.1 degrees, 23.5 degrees, and 26.2 degrees, each of the diffraction angles having an error of about ±0.2 degrees (2θ).

9. The solvate of claim 4, wherein Form II has an X-ray powder diffraction pattern as shown in FIG. 4.

10. The solvate of claim 4, wherein Form II has a DSC profile characterized by an endothermic transition at temperature at about 245.7-247.0° C.

11. The solvate of claim 4, wherein Form II has a DSC profile as shown in FIG. 5.

12. The solvate of claim 4, wherein Form II has a thermogravimetric (TG) profile as shown in FIG. 6.

13. A method of preparing Form II of claim 4, comprising:

(1) mixing compound 6-((6,7-dimethoxyquinazolin-4-yl)oxy)-N, 2-dimethylbenzofuran-3-carboxamide with at least one dissolution solvent, and heating the mixture to reflux to obtain a solution; wherein said dissolution solvent comprises ethanol, or a solvent mixture of ethanol and an aprotic solvent wherein volume percentage of ethanol in the solvent mixture is more than about 65%;

(2) cooling the solution obtained in step (1) to ambient temperature slowly; and (3) isolating Form II of 6-((6, 7-dimethoxyquinazolin-4-yl)oxy)-N, 2-dimethylbenzofuran-3-carboxamide.

14. A method of preparing Form II of claim 4, comprising:

(1) mixing compound 6-((6,7-dimethoxyquinazolin-4-yl)oxy)-N, 2-dimethylbenzofuran-3-carboxamide with at least one dissolution solvent, then heating the mixture to reflux to obtain the first solution; wherein, said dissolution solvent comprises ethanol, or a solvent mixture of ethanol and a weak organic;

(2) adding at least one anti-dissolution solvent to said first solution at refluxing temperature to obtain the second solution, wherein said anti-dissolution solvent comprises $C_{5-8}$ straight or branched alkane;

(3) allowing said second solution to cool to ambient temperature; and (4) isolating Form II of 6-((6,7-dimethoxyquinazolin-4-yl)oxy)-N, 2-dimethylbenzofuran-3-carboxamide.

15. The method of claim 14, wherein alkane is n-heptane.

16. A method of preparing Form II of claim 4, comprising:

(1) suspending compound 6-((6,7-dimethoxyquinazolin-4-yl)oxy)-N, 2-dimethylbenzofuran-3-carboxamide in an appropriate amount of a solvent system; wherein, said solvent system comprises ethanol, a solvent mixture of ethanol and $C_{5-8}$ straight or branched alkane, or a solvent mixture of ethanol and water, wherein volume percentage of ethanol in the solvent mixture of ethanol and water is not less than about 80%;

(2) stirring the suspension obtained in step (1) for a period of time; and (3) isolating to obtain Form II of 6-((6,7-dimethoxyquinazolin-4-yl)oxy)-N, 2-dimethylbenzofuran-3-carboxamide.

17. The method of claim 16, wherein alkane is n-heptane.

18. A method of treating one or more diseases mediated by kinase insert domain-containing receptor (KDR) in a subject in need thereof, comprising administering to the subject an effective amount of Form II of claim 4.

19. The method according to claim 18, wherein the disease is cancer selected from lung cancer, head and neck cancer, pancreatic cancer, colon cancer, breast cancer, ovarian cancer, prostate cancer, stomach cancer, kidney cancer, liver cancer, brain cancer, bone cancer, sarcoma, and leukemia.

20. The method according to claim 18, wherein the disease is metastatic colorectal cancer.

21. A pharmaceutical composition comprising an effective amount of a crystalline Form II of claim 4, and at least one pharmaceutically acceptable carrier.

22. A pharmaceutical composition comprising an effective amount of the crystalline Form II of claim 4, and at least one pharmaceutically acceptable carrier, wherein the content of other crystalline forms in the pharmaceutical composition is less than 40% by weight.

23. The pharmaceutical composition according to claim 22, wherein the content of other crystalline forms in the pharmaceutical composition is less than 30% by weight.

24. The pharmaceutical composition according to claim 22, wherein the content of other crystalline forms in the pharmaceutical composition is less than 20% by weight.

25. The pharmaceutical composition according to claim 22, wherein the content of other crystalline forms in the pharmaceutical composition is less than 10% by weight.

26. The pharmaceutical composition according to claim 22, wherein the content of other crystalline forms in the pharmaceutical composition is less than 5% by weight.

27. The pharmaceutical composition according to claim 22, wherein the content of other crystalline forms in the pharmaceutical composition is less than 1% by weight.

28. A method of treating colorectal cancer in a subject in need thereof, comprising administering to the subject an effective amount of the pharmaceutical composition of claim 22, for treating colorectal cancer.

* * * * *